(12) United States Patent
Vandlik et al.

(10) Patent No.: US 6,709,412 B2
(45) Date of Patent: Mar. 23, 2004

(54) BLOOD PROCESSING SYSTEMS AND METHODS THAT EMPLOY AN IN-LINE LEUKOFILTER MOUNTED IN A RESTRAINING FIXTURE

(75) Inventors: Mark Vandlik, Gurnee, IL (US); Michael J Kast, Evanston, IL (US); Kelly B Smith, Gurnee, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/976,833

(22) Filed: Oct. 13, 2001

(65) Prior Publication Data

US 2002/0090319 A1 Jul. 11, 2002

Related U.S. Application Data

(63) Continuation-in-part of application No. 09/389,504, filed on Sep. 3, 1999.

(51) Int. Cl.[7] .............................................. A61M 37/00
(52) U.S. Cl. .................... 604/6.02; 604/6.03; 604/6.04; 604/6.1; 604/6.11; 210/85; 210/143; 210/782; 210/416.1; 210/257.1; 494/36; 494/43; 494/60; 494/85
(58) Field of Search ..................... 422/44–48; 604/4.01, 604/5.01, 6.01–6.05, 6.07, 6.09, 6.11, 6.15–6.16; 210/645–47, 650, 739, 740–41, 744, 745, 767, 781–82, 784, 787, 85, 87–89, 90, 143, 145–46, 252–56, 257.1–257.2, 258, 282; 128/898, 905, 920, 923, DIG. 3; 494/36, 37, 43, 45, 60, 11, 85

(56) References Cited

U.S. PATENT DOCUMENTS

| | | |
|---|---|---|
| 3,681,899 A | 8/1972 | Grote |
| 4,077,882 A | 3/1978 | Gangemi |
| 4,119,120 A | 10/1978 | Mehaffy et al. |
| 4,285,464 A | 8/1981 | Latham, Jr. |
| 4,410,341 A | 10/1983 | Edwards et al. |
| 4,447,191 A | 5/1984 | Bilstad et al. |
| 4,479,760 A | 10/1984 | Bilstad et al. |
| 4,479,761 A | 10/1984 | Bilstad et al. |

(List continued on next page.)

FOREIGN PATENT DOCUMENTS

| | | |
|---|---|---|
| EP | 0771569 | 5/1997 |
| JP | 2001-149444 | 6/2001 |
| JP | 2003-52808 | 2/2003 |
| WO | WO 95/20985 | 8/1995 |
| WO | WO 96/40319 | 12/1996 |
| WO | WO 96/40328 | 12/1996 |
| WO | WO 97/02059 | 1/1997 |
| WO | WO 97/09074 | 3/1997 |
| WO | WO 98/22163 | 5/1998 |
| WO | WO98/22165 | 5/1998 |

OTHER PUBLICATIONS

Therakos Brochure Circa 1998.

*Primary Examiner*—Patricia Bianco
(74) *Attorney, Agent, or Firm*—Daniel D. Ryan; Bradford R. L. Price; Amy L. H. Rockwell

(57) ABSTRACT

Systems and methods separate blood cells from whole blood and pump the separated blood cells through an in-line leukofilter to a blood cell storage container. The leukofilter has a filtration medium enclosed within a flexile housing. The systems and methods employ a fixture to restrain expansion of the flexible filter housing during operation of the pump. The fixture has a bracket to enable its releasable attachment to the blood processing device employed to carry out the separation process.

6 Claims, 24 Drawing Sheets

U.S. PATENT DOCUMENTS

| | | |
|---|---|---|
| 4,479,762 A | 10/1984 | Bilstad et al. |
| 4,481,827 A | 11/1984 | Bilstad et al. |
| 4,486,189 A | 12/1984 | Troutner et al. |
| 4,526,515 A | 7/1985 | DeVries |
| 4,776,964 A | 10/1988 | Schoendorfer et al. |
| 4,778,451 A | 10/1988 | Kamen |
| 4,808,161 A | 2/1989 | Kamen |
| 4,816,019 A | 3/1989 | Kamen |
| 4,828,543 A | 5/1989 | Weiss et al. |
| 4,858,883 A | 8/1989 | Webster |
| 4,865,584 A | 9/1989 | Epstein et al. |
| 4,954,128 A | 9/1990 | Ford |
| 4,965,846 A | 10/1990 | Williamson, IV |
| 5,062,774 A | 11/1991 | Kramer et al. |
| 5,088,515 A | 2/1992 | Kamen |
| 5,108,367 A | 4/1992 | Epstein et al. |
| 5,178,182 A | 1/1993 | Kamen |
| 5,178,603 A | 1/1993 | Prince |
| 5,193,990 A | 3/1993 | Kamen et al. |
| 5,232,437 A | 8/1993 | Lysaght et al. |
| 5,273,517 A | 12/1993 | Barone et al. |
| 5,311,908 A | 5/1994 | Barone et al. |
| 5,344,568 A | 9/1994 | Kitaevich et al. |
| 5,350,357 A | 9/1994 | Kamen et al. |
| 5,421,823 A | 6/1995 | Kamen et al. |
| 5,431,626 A | 7/1995 | Bryant et al. |
| 5,437,624 A | 8/1995 | Langley |
| 5,438,510 A | 8/1995 | Bryant et al. |
| 5,462,416 A | 10/1995 | Dennehey et al. |
| 5,474,683 A | 12/1995 | Bryant et al. |
| 5,482,440 A | 1/1996 | Dennehey et al. |
| 5,588,816 A | 12/1996 | Abbott et al. |
| 5,593,290 A | 1/1997 | Greisch et al. |
| 5,628,908 A | 5/1997 | Kamen et al. |
| 5,634,896 A | 6/1997 | Bryant et al. |
| 5,651,766 A | 7/1997 | Kingsley et al. |
| 5,676,644 A | 10/1997 | Toavs et al. |
| 5,690,815 A | 11/1997 | Krasnoff et al. |
| 5,722,947 A | 3/1998 | Jeppsson et al. |
| 5,738,796 A * | 4/1998 | Bormann et al. ........... 210/806 |
| 5,746,708 A * | 5/1998 | Giesler et al. ............ 604/6.11 |
| 5,746,719 A | 5/1998 | Farra et al. |
| 5,755,683 A | 5/1998 | Houle et al. |
| 5,762,791 A | 6/1998 | Deniega et al. |
| 5,769,811 A | 6/1998 | Stacey et al. |
| 5,795,317 A | 8/1998 | Brierton et al. |
| 5,871,693 A | 2/1999 | Lindsay |
| 5,921,951 A | 7/1999 | Morris |
| 5,938,634 A | 8/1999 | Packard |
| 5,951,509 A | 9/1999 | Morris |
| 5,954,971 A * | 9/1999 | Pages et al. ................ 210/739 |
| 5,989,438 A | 11/1999 | Fumiyama |
| 6,071,423 A | 6/2000 | Brown et al. |
| 6,106,498 A | 8/2000 | Friedli et al. |
| 6,106,727 A | 8/2000 | Krasnoff et al. |
| RE36,871 E | 9/2000 | Epstein et al. |
| 6,322,709 B1 | 11/2001 | Krasnoff et al. |

* cited by examiner

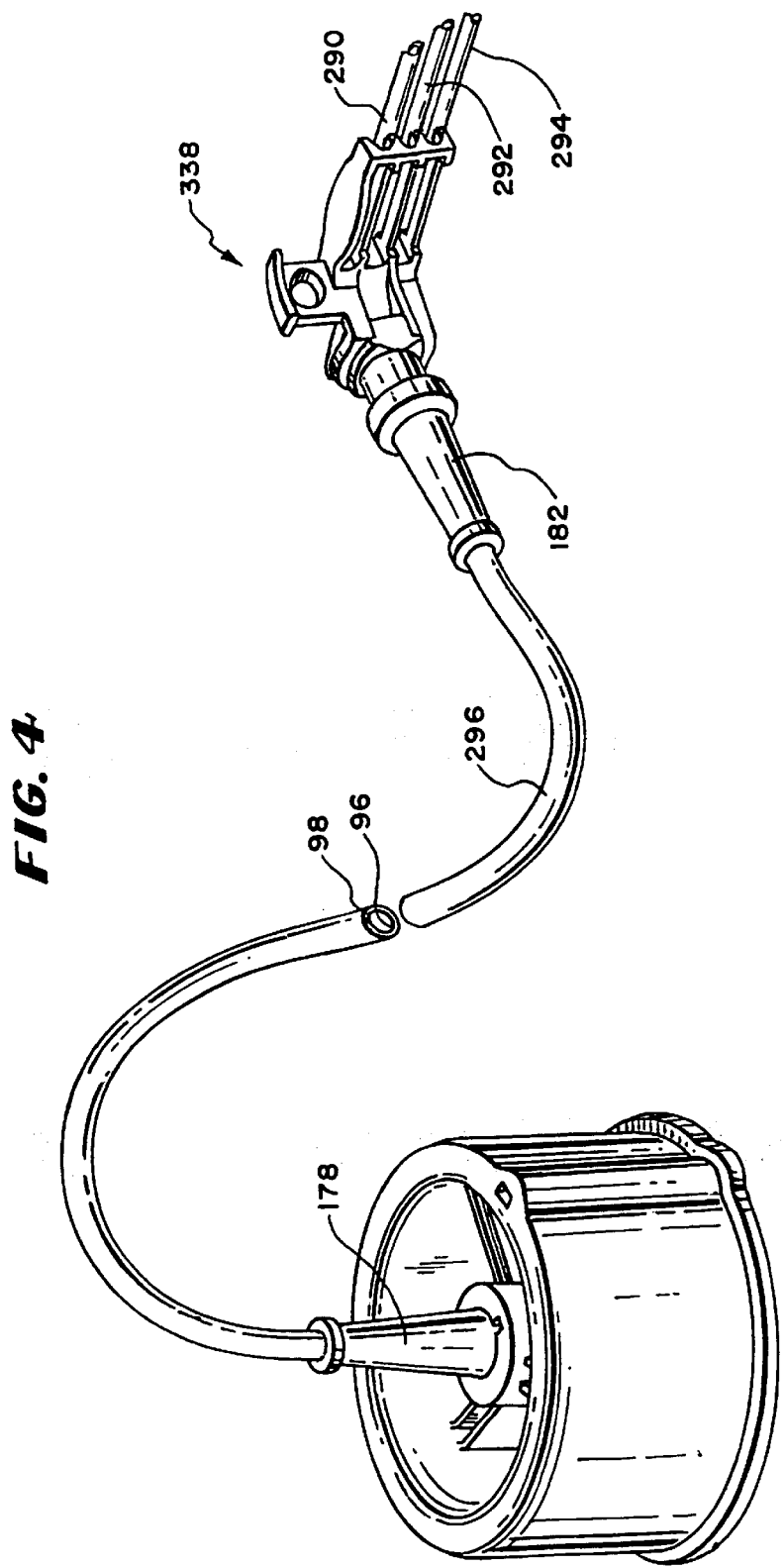

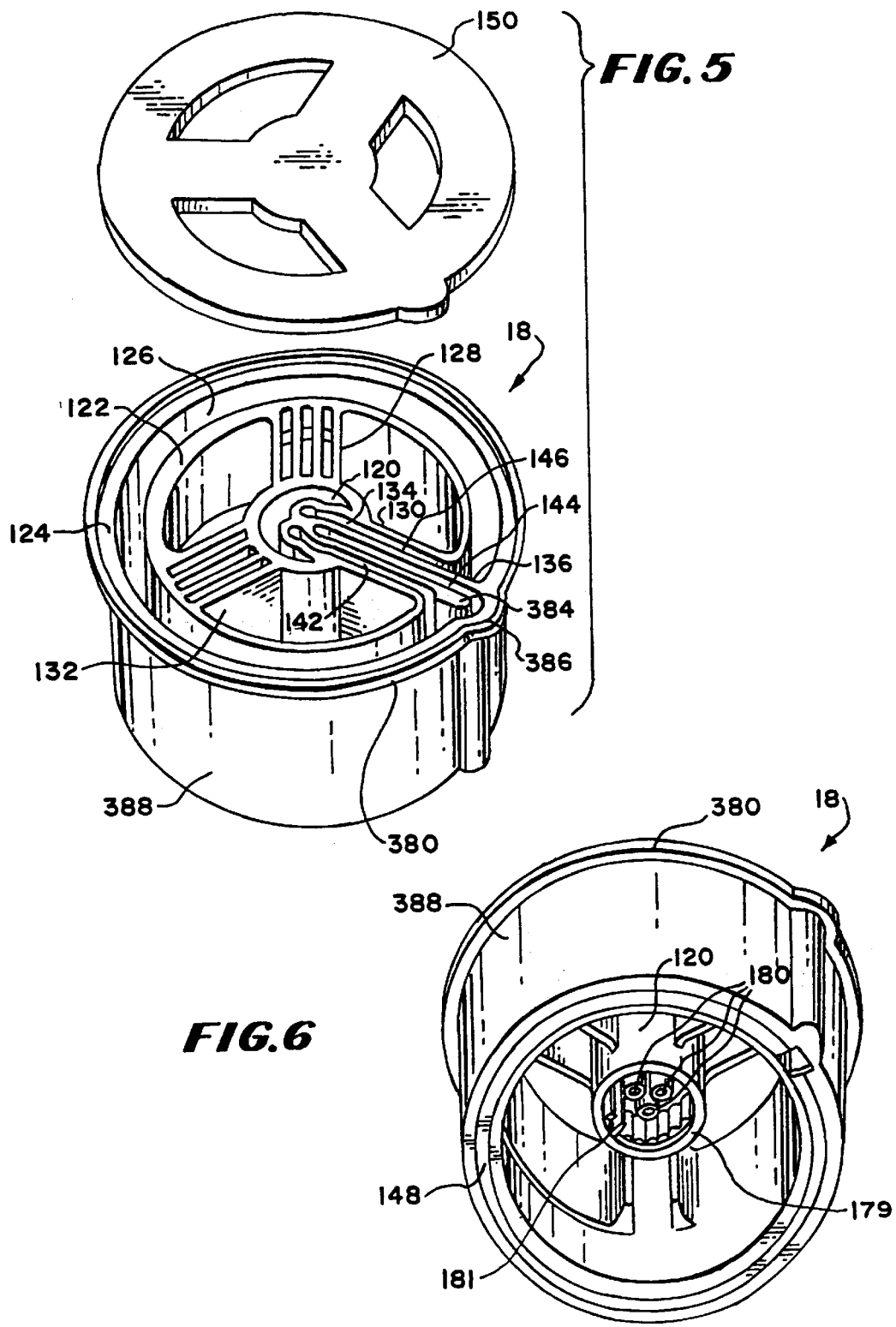

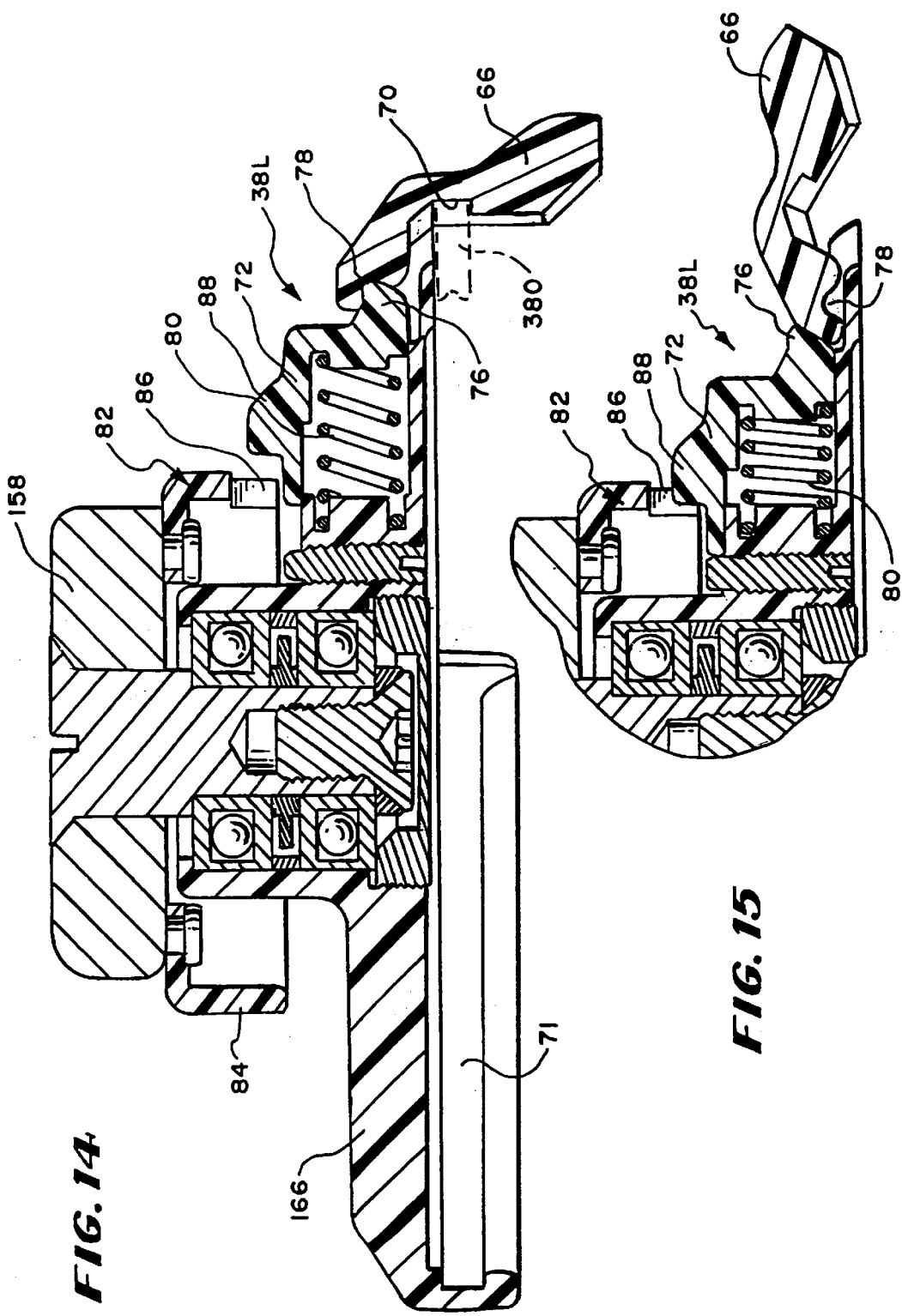

FROM RED BLOOD CELL RESERVOIR 308

TO RED BLOOD CELL STORAGE CONTAINERS 307/309

BLOOD PROCESSING SYSTEMS AND METHODS THAT EMPLOY AN IN-LINE LEUKOFILTER MOUNTED IN A RESTRAINING FIXTURE

RELATED APPLICATION

This application is a continuation-in-part of co-pending U.S. patent application Ser. No. 09/389,504, filed Sep. 3, 1999, and entitled "Blood Separation Systems and Methods Using a Multiple Function Pump Station to Perform Different On-Line Processing Tasks," which is incorporated herein by reference.

FIELD OF THE INVENTION

This invention relates to systems and methods for processing and collecting blood, blood constituents, or other suspensions of cellular material.

BACKGROUND OF THE INVENTION

Today people routinely separate whole blood, usually by centrifugation, into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Conventional blood centrifuges are of a size that does not permit easy transport between collection sites. Furthermore, loading and unloading operations can sometimes be time consuming and tedious.

In addition, a need exists for further improved systems and methods for collecting blood components in a way that lends itself to use in high volume, on line blood collection environments, where higher yields of critically needed cellular blood components, like plasma, red blood cells, and platelets, can be realized in reasonable short processing times.

The operational and performance demands upon such fluid processing systems become more complex and sophisticated, even as the demand for smaller and more portable systems intensifies. The need therefore exists for automated blood processing controllers that can gather and generate more detailed information and control signals to aid the operator in maximizing processing and separation efficiencies.

SUMMARY OF THE INVENTION

The invention provides systems and methods for processing blood and blood constituents that lend themselves to portable, flexible processing platforms equipped with straightforward and accurate control functions. One aspect of the invention provides a blood processing system comprising a blood processing set and a blood processing device.

The blood processing set includes a donor flow channel to convey blood from a donor. The set also includes a blood processing flow channel including a blood separation chamber to centrifugally separate blood cells from donor whole blood. The set further includes a blood component collection flow channel including a blood cell storage container and an in-line filter to remove leukocytes from the blood cells before entering the blood cell storage container. The in-line filter includes a flexible housing that encloses a filter medium.

The blood processing device includes a pump station adapted to be placed into communication with the donor flow channel, the blood processing flow channel, and the blood component collection flow channel. The device also includes a centrifuge station adapted to support the blood separation chamber and to rotate the blood separation chamber. The device further includes a controller to operate the pump station in multiple modes. One mode is a processing mode, during which the pump station is operated to convey whole blood in the donor flow channel into the blood processing flow channel for separation of the blood cells in the blood separation chamber. Another mode is a collection mode, during which the pump station is operated to convey at least some of the blood cells in the blood processing flow channel into the blood component collection flow channel for on-line removal of leukocytes and collection in the blood cell storage container.

The system also includes a fixture to restrain expansion of the filter housing during operation of the pump station in the collection mode. The fixture includes a bracket to enable releasable attachment of the fixture to the blood processing device.

Other features and advantages of the inventions are set forth in the following specification and attached drawings.

BRIEF DESCRIPTION OF THE DRAWINGS

FIG. 4 is a perspective view of a blood processing chamber and associated fluid conveying umbilicus that form a part of the fluid processing set shown in FIGS. 1 and 2;

FIG. 5 is an exploded top perspective view of the of a two-part molded centrifugal blood processing container, which can form a part of the fluid processing set used in association with the device shown in FIGS. 1 and 2;

FIG. 6 is a bottom perspective view of the molded processing container shown in FIG. 5;

FIG. 14 is a side section view of the rotor plate shown in FIG. 13, showing the components of the latching assembly as positioned when the latch assembly is in its chamber retaining position;

FIG. 15 is a side section view of the rotor plate shown in FIG. 13, showing the components of the latching assembly as positioned when the latch assembly is in its chamber releasing position;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
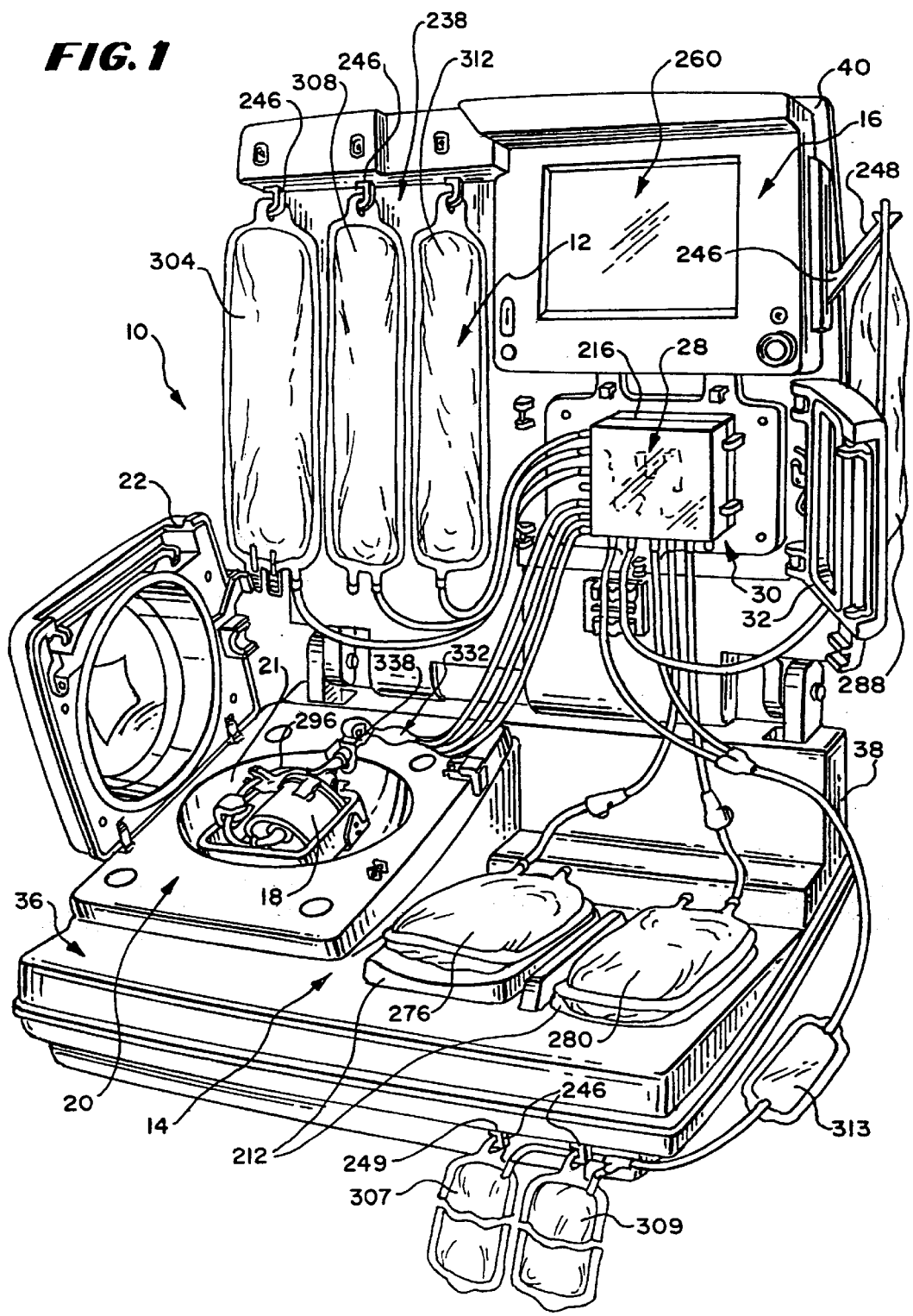
FIG. 1 is a perspective view of a fluid processing system that embodies features of the invention, with the doors to the centrifuge station and pump and valve station being shown open to accommodate mounting of a fluid processing set.

FIG. 1 shows a fluid processing system 10 that embodies the features of the invention. The system 10 can be used for processing various fluids.

The system 10 is particularly well suited for processing whole blood and other suspensions of biological cellular materials. Accordingly, the illustrated embodiment shows the system 10 used for this purpose.

I. System Overview

The system 10 includes three principal components. These are: (i) a liquid and blood flow set 12 (shown schematically in FIG. 3); (ii) a blood processing device 14 (see FIGS. 1 and 2), which interacts with the flow set 12 to cause separation and collection of one or more blood components; and (iii) a controller 16 carried on board the device 14, which governs the interaction to perform a blood processing and collection procedure selected by the operator.

A. The Processing Device and Controller

The blood processing device 14 and controller 16 are intended to be durable items capable of long term use. In the illustrated and preferred embodiment, the blood processing device 14 and controller 16 are mounted inside a portable housing or case 36. The case 36 presents a compact footprint, suited for set up and operation upon a table top or other relatively small surface. The case 36 is also intended to be transported easily to a collection site.

The case 36 includes a base 38 and a hinged lid 40, which opens for use (as FIG. 1 shows). In use, the base 38 is intended to rest in a generally horizontal support surface. The lid 40 also closes for transport (see FIG. 26).

The case 36 can be formed into a desired configuration, e.g., by molding. The case 36 is preferably made from a lightweight, yet durable, plastic material.

The controller 16 carries out process control and monitoring functions for the system 10. The controller 16 comprises a main processing unit (MPU), which can comprise, e.g., a Pentium™ type microprocessor made by Intel Corporation, although other types of conventional microprocessors can be used. The MPU can be mounted inside the lid 40 of the case 36.

Preferably, the controller 16 also includes an interactive user interface 260, which allows the operator to view and comprehend information regarding the operation of the system 10. In the illustrated embodiment, the interface 260 includes an interface screen carried in the lid 40, which displays information for viewing by the operator in alpha-numeric format and as graphical images.

Further details of the controller 16 can be found in Nayak et al, U.S. Pat. No. 6,261,065, which is incorporated herein by reference. Further details of the interface can be found in Lyle et al, U.S. Pat. No. 5,581,687, which is also incorporated herein by reference.

Figure 26:
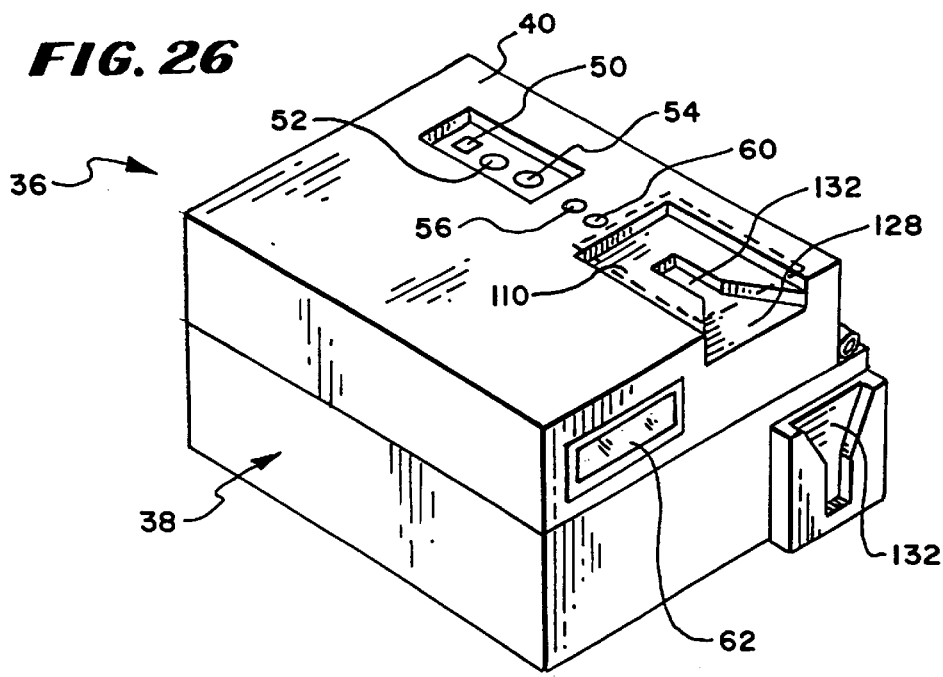
FIG. 26 is a perspective view of a device of a type of shown in FIGS. 1 and 2, with the lid of the device closed to also reveal the location of various components and a leukofilter holder carried on the exterior of the lid.

As FIG. 26 shows, the lid 40 can be used to support other input/outputs to couple other external devices to the controller 16 or other components of the device 14. For example, an ethernet port 50, or an input 52 for a bar code reader or the like (for scanning information into the controller 16), or a diagnostic port 54, or a port 56 to be coupled to a pressure cuff 58 (see FIG. 3), or a system transducer calibration port 60, can all be conveniently mounted for access on exterior of the lid 40, or elsewhere on the case 36 of the device 14.

B. The Flow Set

Figure 2:
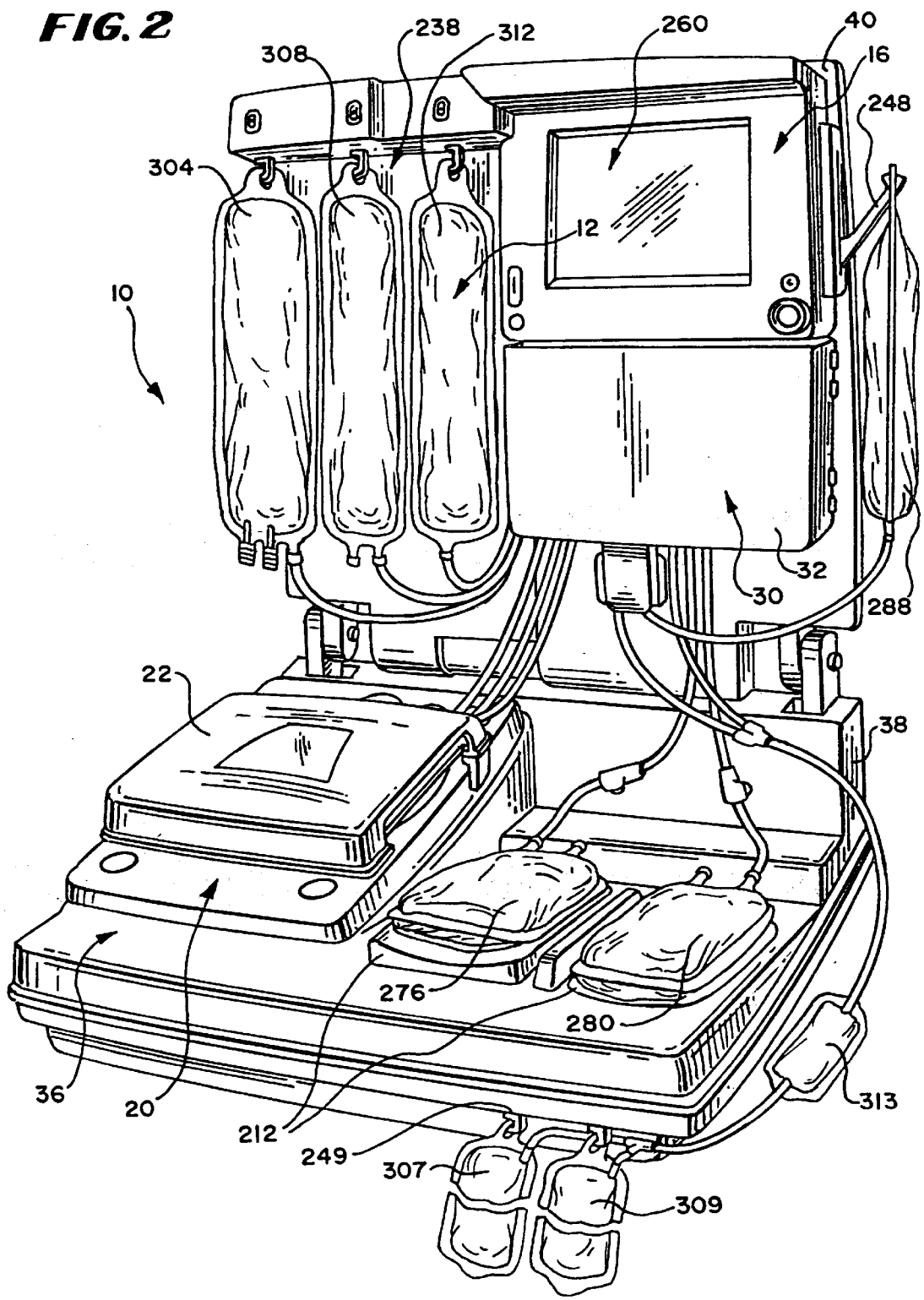
FIG. 2 is a perspective view of the system shown in FIG. 1, with the doors to the centrifuge station and pump and valve station being shown closed as they would be during fluid processing operations.

The flow set 12 (see FIG. 3), is intended to be a sterile, single use, disposable item. Before beginning a given blood processing and collection procedure, the operator loads various components of the flow set 12 in the case 36 in association with the device 14 (as FIGS. 1 and 2 show). The controller 16 implements the procedure based upon preset protocols, taking into account other input from the operator. Upon completing the procedure, the operator removes the flow set 12 from association with the device 14.

The portion of the set 12 holding the collected blood component or components are removed from the case 36 and retained for storage, transfusion, or further processing. The remainder of the set 12 is removed from the case 36 and discarded.

The flow set 12 can take various forms. In the illustrated embodiment (see FIGS. 1 and 3), the flow set includes a blood processing chamber 18 designed for use in association with a centrifuge. Accordingly, the processing device 14 includes a centrifuge station 20 (see FIG. 1), which receives the processing chamber 18 for use (see FIG. 12).

As FIG. 1 shows, the centrifuge station 20 comprises a compartment 21 formed in the base 38. The centrifuge station 20 includes a door 22, which opens and closes the compartment 21. The door 22 opens (as FIG. 1 shows) to allow loading of the processing chamber 18 into the compartment 21. The door 22 closes (as FIG. 2 shows) to enclose the processing chamber 18 within the compartment 21 during operation.

The centrifuge station 20 rotates the processing chamber 18. When rotated, the processing chamber 18 centrifugally separates whole blood received from a donor into component parts, e.g., red blood cells, plasma, and platelets.

Figure 29:
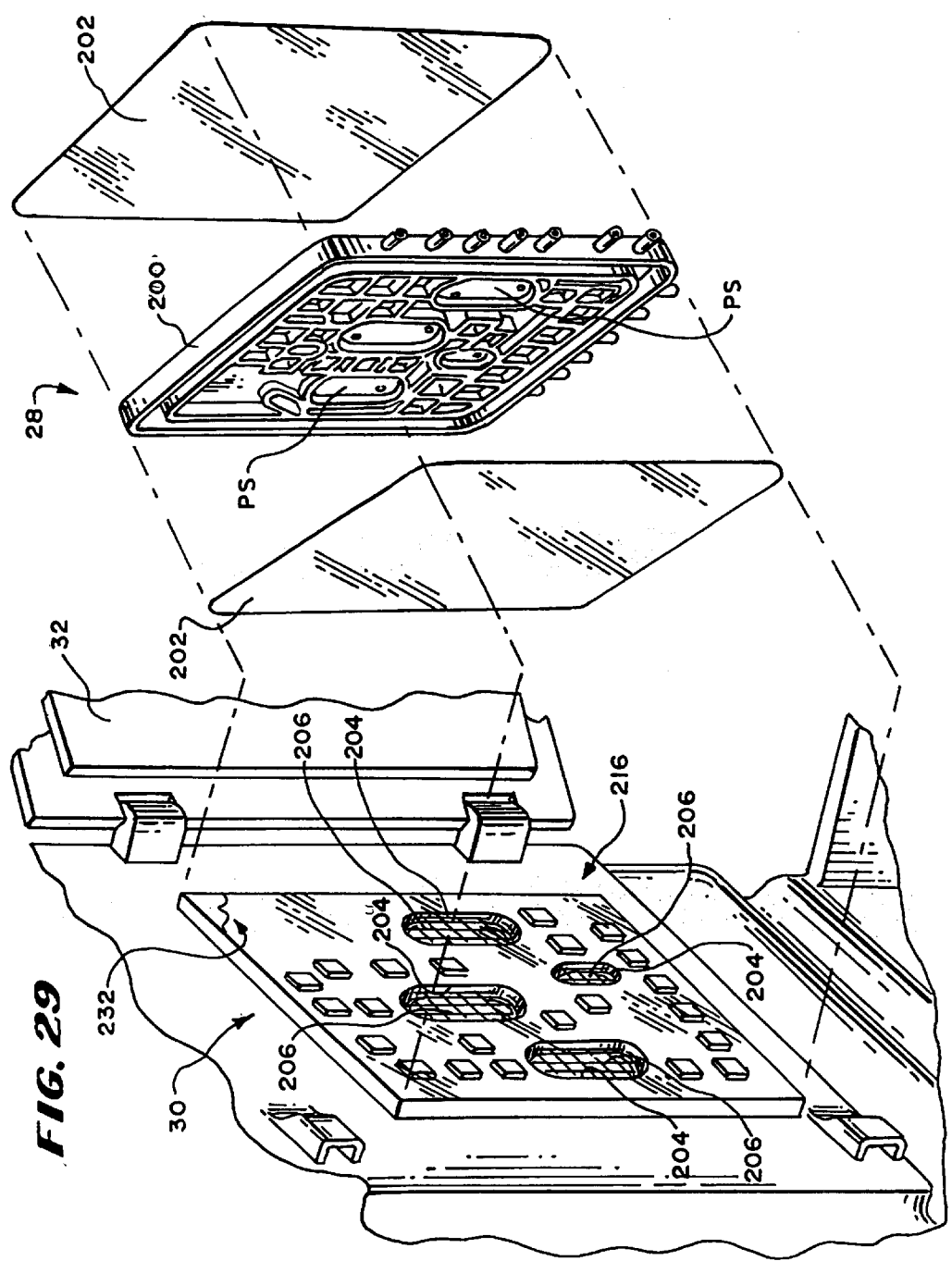
FIG. 29 is an exploded perspective view of a cassette, which can form a part of the processing set used in association with the processing device shown in FIGS. 1 and 2, and the pump and valve station on the processing device, which receives the cassette for use.

In the illustrated embodiment, the set 12 also includes a fluid pressure actuated cassette 28 (see FIG. 29). The cassette 28 provides a centralized, programmable, integrated platform for all the pumping and valving functions required for a given blood processing procedure. In the illustrated embodiment, the fluid pressure comprises positive and negative pneumatic pressure. Other types of fluid pressure can be used.

The cassette 28 can take various forms. In a preferred embodiment (see FIG. 29), the cassette 28 comprises an injection molded body 200 made of a rigid medical grade plastic material. Flexible diaphragms 202, preferably made of flexible sheets of medical grade plastic, overlay the front side and back sides of the cassette 28. The diaphragms are sealed about their peripheries to the peripheral edges of the front and back sides of the cassette 28.

Figure 3:
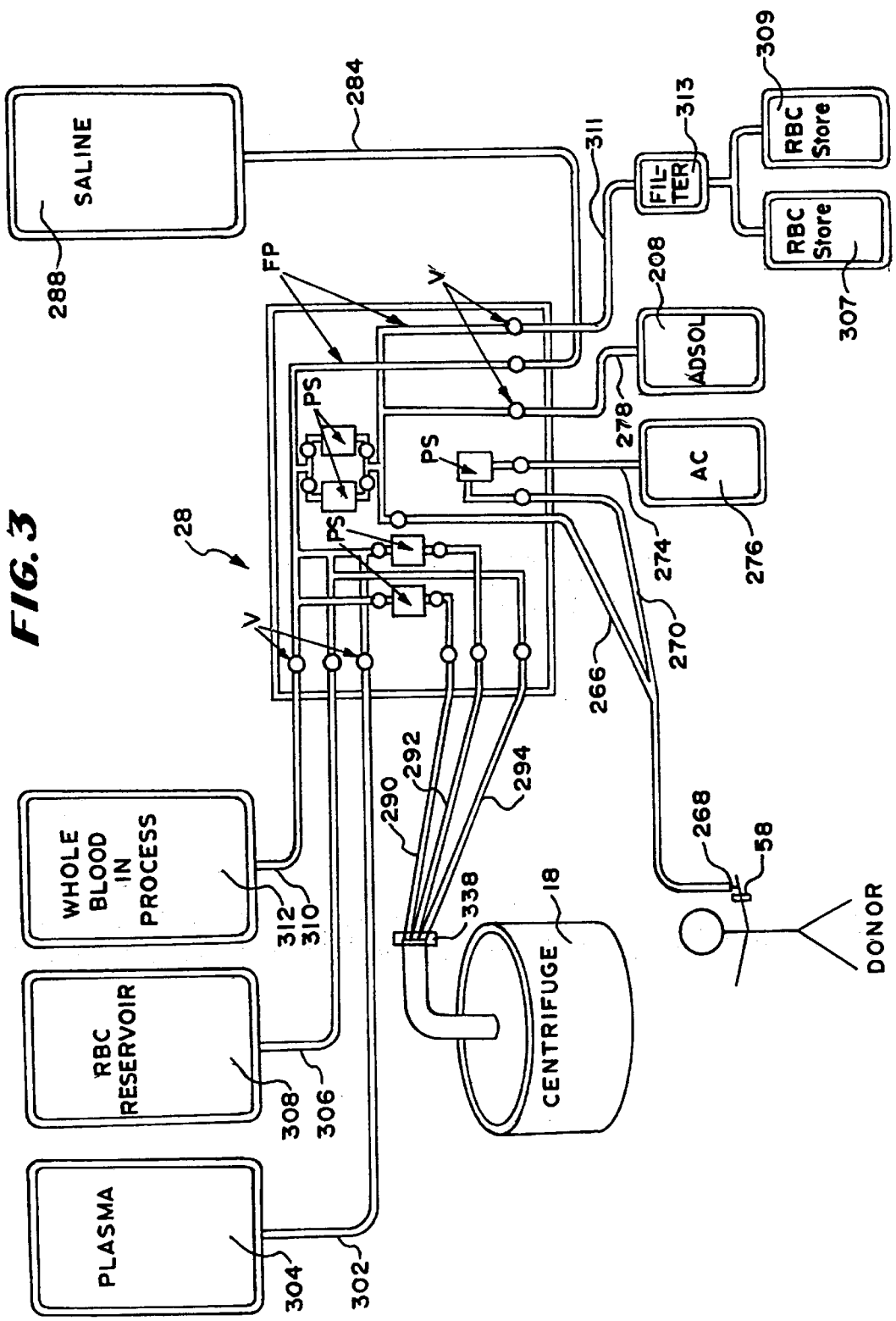
FIG. 3 is a schematic view of a representative blood processing circuit formed by the fluid processing set shown in FIGS. 1 and 2.

As FIG. 29 shows, the cassette 28 has an array of interior cavities formed on both the front and back sides The interior cavities define pneumatic pump stations (schematically designated PS in FIG. 3), which are interconnected by a pattern of fluid flow paths (schematically designated FP in FIG. 3) through an array of in line, pneumatic valves (schematically designated V in FIG. 3).

As FIGS. 1 and 29 show, the cassette 28 interacts with a pneumatic actuated pump and valve station 30, which is mounted in the lid of the 40 of the case 36. The pump and valve station 30 includes a cassette holder 216. A door 32 is hinged to move with respect to the cassette holder 216 between an opened position, exposing the cassette holder 216 (shown in FIG. 1) for loading and unloading the cassette 28, and a closed position, enclosing the cassette 28 within the pump and valve station 30 for use (shown in FIG. 2). The pump and valve station 30 includes pneumatic actuator ports 204 (see FIG. 29) that apply positive and negative pneumatic pressure upon the diaphragms of the cassette 28. The pneumatic pressures displace the diaphragms 202 with respect to the pump chambers and valves, to thereby direct liquid flow through the cassette 28.

Further details of the cassette 28 and the operation of the pump and valve station 30 can be found in Nayak et al, U.S. Pat. No. 6,261,065, which is incorporated herein by reference.

Referred back to FIG. 3, the flow set 16 also includes an array of tubes and containers in flow communication with the cassette 28. The arrangement of tubes and containers can vary according to the processing objectives. The system 10 can be operated to collect red blood cells, plasma, red blood cells and plasma, and platelets.

In the illustrated embodiment, the flow set 16 is arranged to support the centrifugal collection of two units of red blood cells (about 360 ml), and to filter the red blood cells to reduce the number of leukocytes prior to storage. During this procedure, whole blood from a donor is centrifugally processed in the chamber 18 into red blood cells (in which a majority of the leukocytes resides) and a plasma constituent (in which a majority of the platelets resides). The plasma constituent is returned to the donor, while the targeted volume of red blood cells is collected, filtered to reduce the population of leukocytes, and placed into containers for storage mixed with a red blood cell storage solution.

In this configuration (see FIG. 3), the flow set 16 includes a donor tube 266 having an attached phlebotomy needle 268. The donor tube 266 is coupled to a port of the cassette 28.

As FIG. 3 shows, a pressure cuff 58 is desirable used to enhance venous blood flow through the phlebotomy needle 268 during blood processing. The pressure cuff 58 is coupled to the pressure cuff port 56 on the lid 40 (as previously described), and the pressure supplied to the cuff 58 is desirably controlled by the controller 16. The controller 16 can also operate a vein pressure display 62 (see FIG. 26), which shows vein pressure at the pressure cuff 56.

An anticoagulant tube 270 is coupled to the phlebotomy needle 268. The anticoagulant tube 270 is coupled to another cassette port. A container 276 holding anticoagulant is coupled via a tube 274 to another cassette port.

A container 288 holding saline is coupled via a tube 284 to another cassette port.

The set 16 further includes tubes 290, 292, 294, which extend to an umbilicus 296. When installed in the processing station, the umbilicus 296 links the rotating processing chamber 18 with the cassette 28 without need for rotating seals. In a preferred embodiment, the umbilicus 296 is made from rotational-stress-resistant Hytrel® copolyester elastomers (DuPont). Further details of the construction of the umbilicus 296 will be provided later.

The tubes 290, 292, and 294 are coupled, respectively, to other cassette ports. The tube 290 conveys whole blood into the processing chamber 18. The tube 292 conveys plasma constituent from the processing chamber 18. The tube 294 conveys red blood cells from processing chamber 18.

A plasma collection reservoir 304 is coupled by a tube 302 to a cassette port. The collection reservoir 304 is intended, in use, to serve as a reservoir for the plasma constituent during processing prior to its return to the donor.

A red blood cell collection reservoir 308 is coupled by a tube 306 to a cassette port. The collection reservoir 308 is intended, in use, to receive red blood cells during processing for storage.

Two red blood cell storage containers 307 and 309 are coupled by a tube 311 to another cassette port. A leukocyte reduction filter 313 is carried in line by the tube 311. During processing, red blood cells are transferred from the red blood cell collection reservoir 308 through the filter 313 into the storage containers 307 and 309.

A container 208 holding a red blood cell storage or additive solution is coupled via a tube 278 to another cassette port. The red blood cell storage solution is metered into the red blood cells as they are conveyed from the container 308, through the filter 313, into the storage containers 307 and 309. Further details of this aspect of the collection process will be described later.

A whole blood reservoir 312 is coupled by a tube 310 to a cassette port. The collection container 312 is intended, in use, to serve as a reservoir for whole blood during processing.

Figure 12:
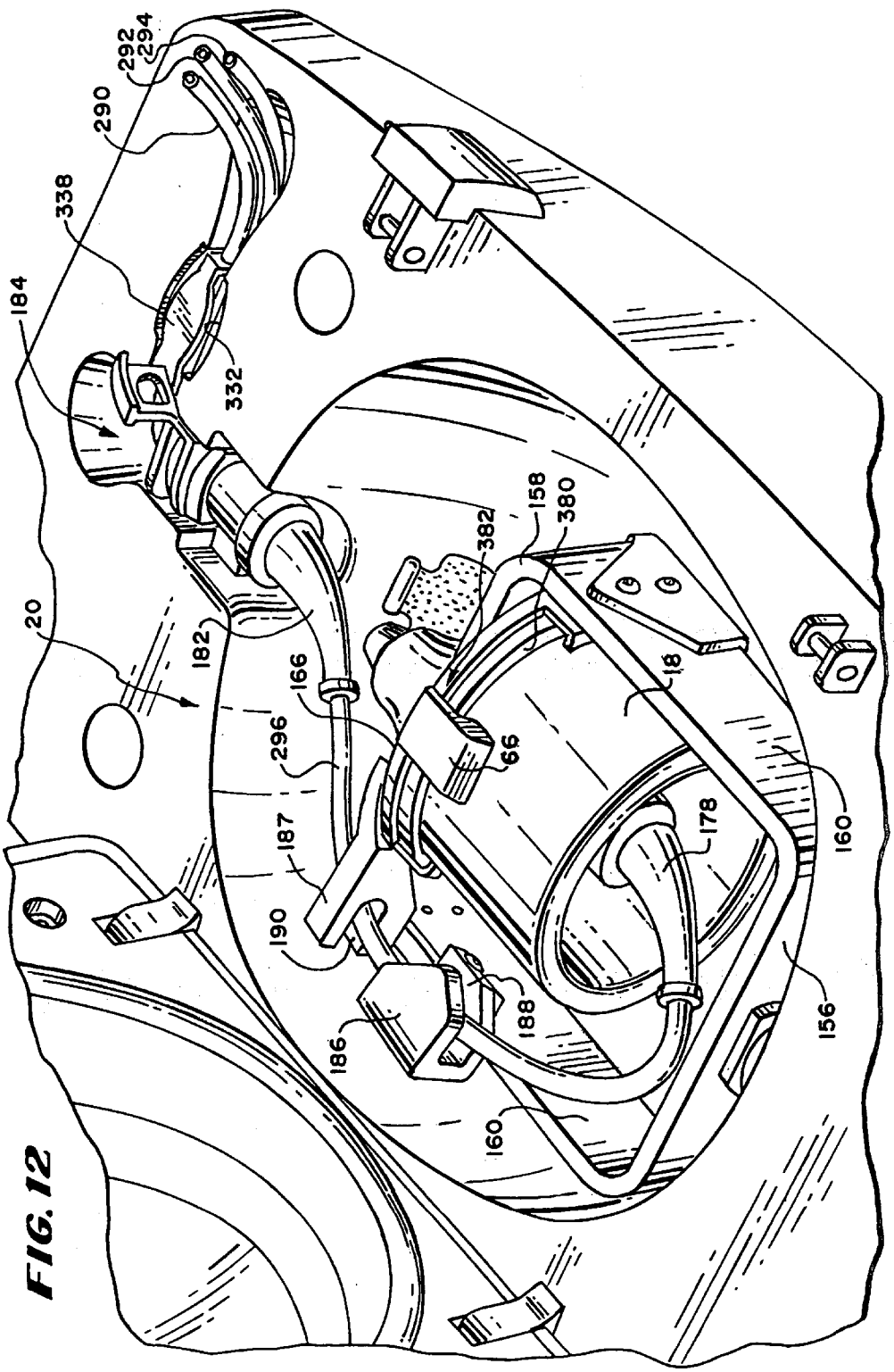
FIG. 12 is a perspective view of the centrifuge assembly fully assembled and housed in the centrifuge station of the device shown in FIGS. 1 and 2, with the blood processing chamber and associated umbilicus also mounted on the centrifuge assembly for use.

In the illustrated embodiment, the set 16 further includes a fixture 338 (see FIG. 4) to hold the tubes 292 and 294 in viewing alignment with an optical sensing station 332 in the base 36 (see FIG. 12). The sensing station 332 optically monitors the presence or absence of targeted blood components (e.g., platelets and red blood cells) conveyed by the tubes 292 and 294. The sensing station 332 provides output reflecting the presence or absence of such blood components. This output is conveyed to the controller 16. The controller 16 processes the output and generates signals to control processing events based, in part, upon the optically sensed events. Further details of the operation of the controller to control processing events based upon optical sensing can be found in Nayak et al, U.S. Pat. No. 6,261,065, which is incorporated herein by reference.

As FIG. 12 shows, the sensing station 332 is desirably located within the confines of the centrifuge station 20. This arrangement minimizes the fluid volume of components leaving the chamber before monitoring by the sensing station 332.

The fixture 338 gathers the tubes 292 and 294 in a compact, organized, side-by-side array, to be placed and removed as a group in association with the sensing station 332. In the illustrated embodiment, the fixture 338 also holds the tube 290, which conveys whole blood into the processing chamber 18, even though no associated sensor is provided. The fixture 338 serves to gather and hold all tubes 290, 292, and 294 that are coupled to the umbilicus 296 in a compact and easily handled bundle.

The fixture 338 can be an integral part of the umbilicus 296, formed, e.g., by over molding. Alternatively, the fixture 338 can be a separately fabricated part, which snap fits about the tubes 290, 292, and 294 for use.

As FIGS. 1 and 2 also show, the case 36 contains other components compactly arranged to aid blood processing. In addition to the centrifuge station 20 and pump and valve station 30, already described, the case 36 includes a weigh station 238 and one or more trays 212 or hangers 248 for containers. The arrangement of these components in the case 36 can vary.

In the illustrated embodiment, the weigh station 238 comprises a series of container hangers/weigh sensors 246 arranged along the top of the lid 40. In use, the containers 304, 308, 312 are suspended on the hangers/weigh sensors 246.

The holding trays 212 comprise molded recesses in the base 38. The trays 212 accommodate the containers 276 (containing anticoagulant) and 208 (containing the red blood cell additive solution). In the illustrated embodiment, an additional swing-out side hanger 248 is also provided on the side of the lid 40. The hanger 248 (see FIG. 2) supports the container 288 (containing saline) during processing. Other swing out hangers 249 support the red blood cells storage containers 307 and 309.

In the illustrated embodiment, the tray 212 holding the container 276 and the hanger 248 also include weigh sensors 246.

As blood or liquids are received into and/or dispensed from the containers during processing, the weigh sensors 246 provide output reflecting weight changes over time. This output is conveyed to the controller 16. The controller 16 processes the incremental weight changes to derive fluid processing volumes. The controller generates signals to control processing events based, in part, upon the derived processing volumes. Further details of the operation of the controller to control processing events can be found in Nayak et al, U.S. Pat. No. 6,261,065, which is incorporated herein by reference.

C. The Centrifugal Processing Chamber

Figure 7:
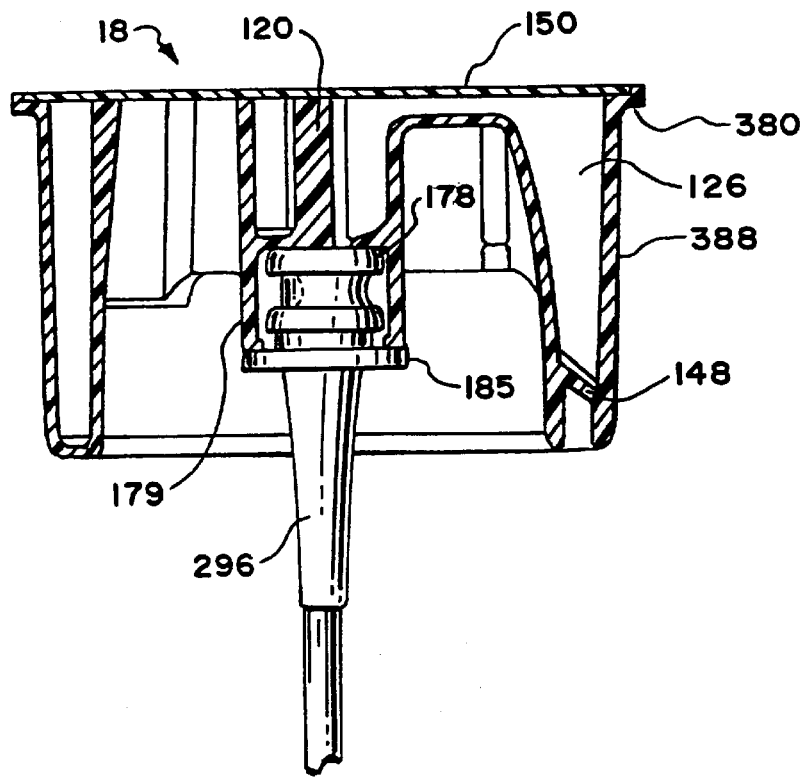
FIG. 7 is a side section view of the molded processing container shown in FIG. 5, after connection of an umbilicus.

FIGS. 5 to 7 show an embodiment of the centrifugal processing chamber 18, which can be used in association with the system 10 shown in FIG. 1 to perform the intended red blood cell collection procedure. In the illustrated embodiment, the processing chamber 18 is preformed in a desired shape and configuration, e.g., by injection molding, from a rigid, biocompatible plastic material, such as a non-plasticized medical grade acrilonitrile-butadiene-styrene (ABS).

In one arrangement, the chamber 18 can be fabricated in two separately molded pieces; namely (as FIGS. 5 to 7 show), a base 388 and a lid 150. The base 388 includes a center hub 120. The hub 120 is surrounded radially by inside and outside annular walls 122 and 124. Between them, the inside and outside annular walls 122 and 124 define a circumferential blood separation channel 126. A molded annular wall 148 closes the bottom of the channel 126.

The top of the channel 126 is closed by the separately molded, flat lid 150 (which is shown separated in FIG. 5 for the purpose of illustration). During assembly (see FIG. 7), the lid 150 is secured to the top of the chamber 18, e.g., by use of a cylindrical sonic welding horn.

All contours, ports, channels, and walls that affect the blood separation process may be preformed in the base 388 in a single, injection molded operation, during which molding mandrels are inserted and removed through the open end of the base 388 (shown in FIG. 5). The lid 150 comprises a simple flat part that can be easily welded to the open end of the base 388 to close it after molding. Because all features that affect the separation process are incorporated into one injection molded component, any tolerance differences between the base 388 and the lid 150 will not affect the separation efficiencies of the chamber 18.

The contours, ports, channels, and walls that are preformed in the base 388 may create surfaces within the base 388 that do not readily permit the insertion and removal of molding mandrels through a single end of the base 388. In this arrangement, the base 388 can be formed by separate molded parts, either by nesting cup shaped subassemblies or two symmetric halves.

Figure 8:
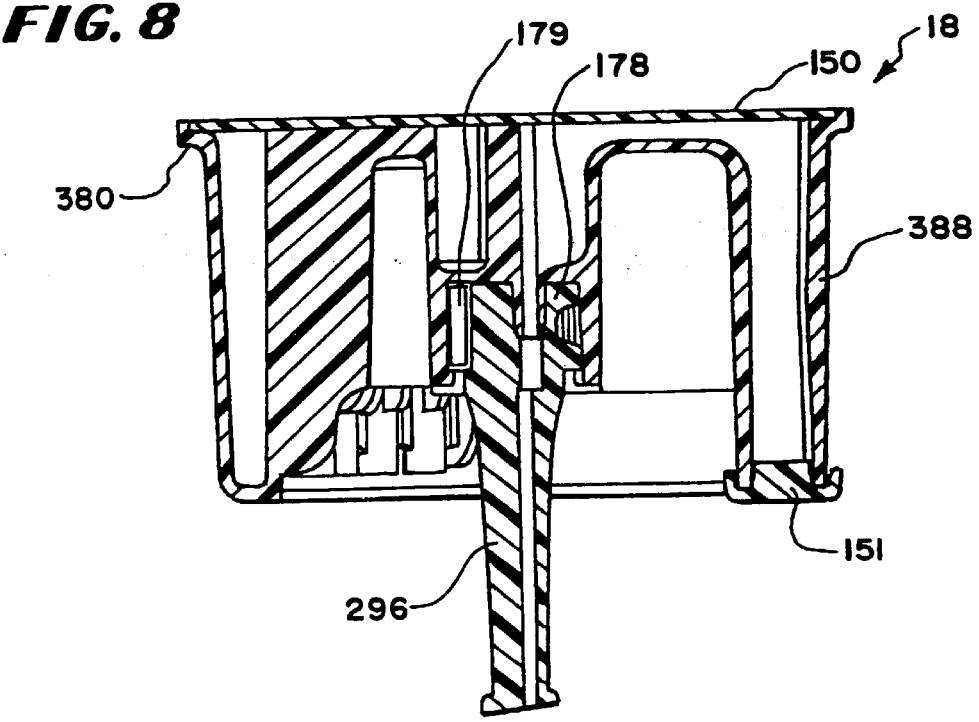
FIG. 8 is a side section view of a three-part molded centrifugal blood processing container which can form a part of the fluid processing set used in association with the device shown in FIGS. 1 and 2.

Alternatively, molding mandrels can be inserted and removed from both ends of the base 388. In this arrangement (see FIG. 8), the chamber 18 can be molded in three pieces; namely, the base 388, the lid 150 (which closes one end of the base 388 through which top molding mandrels are inserted and removed), and a separately molded insert 151 (which closes the other end of the base 388 through which bottom molding mandrels are inserted and removed.

The contours, ports, channels, and walls that are preformed in the base 388 can vary.

Figure 9:
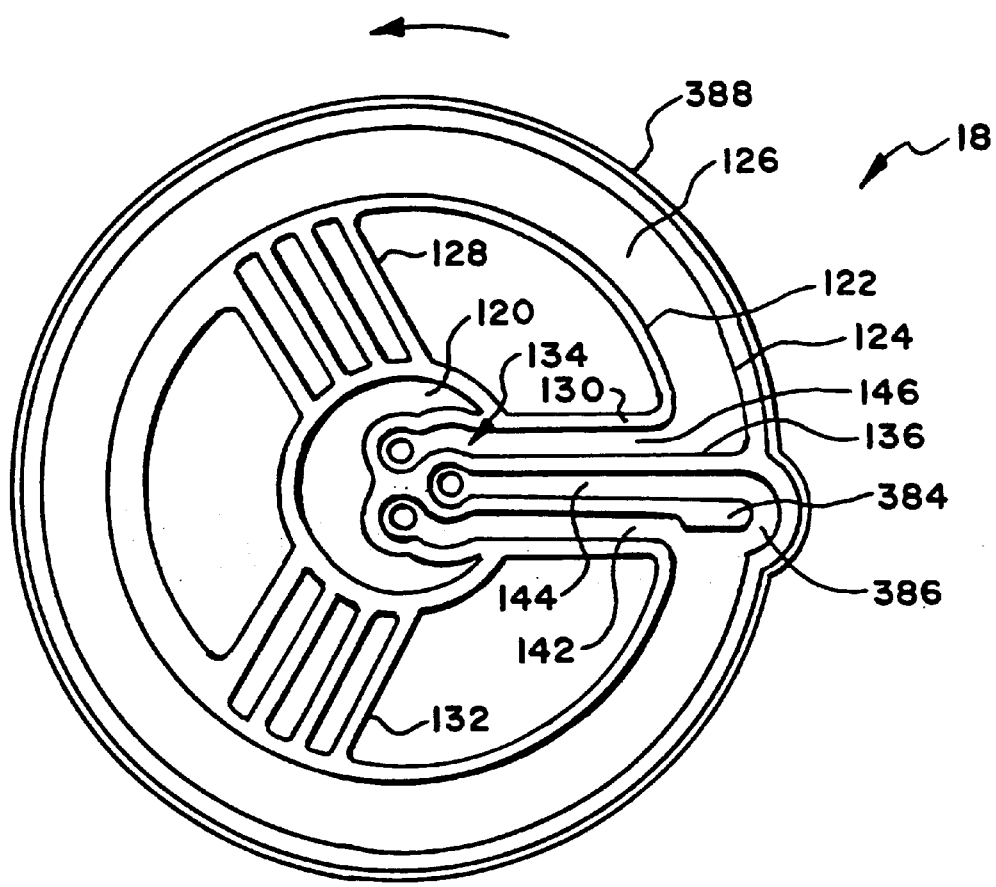
FIG. 9 is a top view of the molded processing container shown in FIG. 5, showing certain details of the separation channel.

As seen in FIG. 9, in one arrangement, the inside annular wall 122 is open between one pair of stiffening walls. The opposing stiffening walls form an open interior region 134 in the hub 120, which communicates with the channel 126. Blood and fluids are introduced from the umbilicus 296 into and out of the separation channel 126 through this region 134.

In this embodiment (as FIG. 9 shows), a molded interior wall 136 formed inside the region 134 extends entirely across the channel 126, joining the outside annular wall 124. The wall 136 forms a terminus in the separation channel 126, which interrupts flow circumferentially along the channel 126 during separation.

Additional molded interior walls divide the region 134 into three passages 142, 144, and 146. The passages 142, 144, and 146 extend from the hub 120 and communicate with the channel 126 on opposite sides of the terminus wall 136. Blood and other fluids are directed from the hub 120 into and out of the channel 126 through these passages 142, 144, and 146.

Figure 24A:
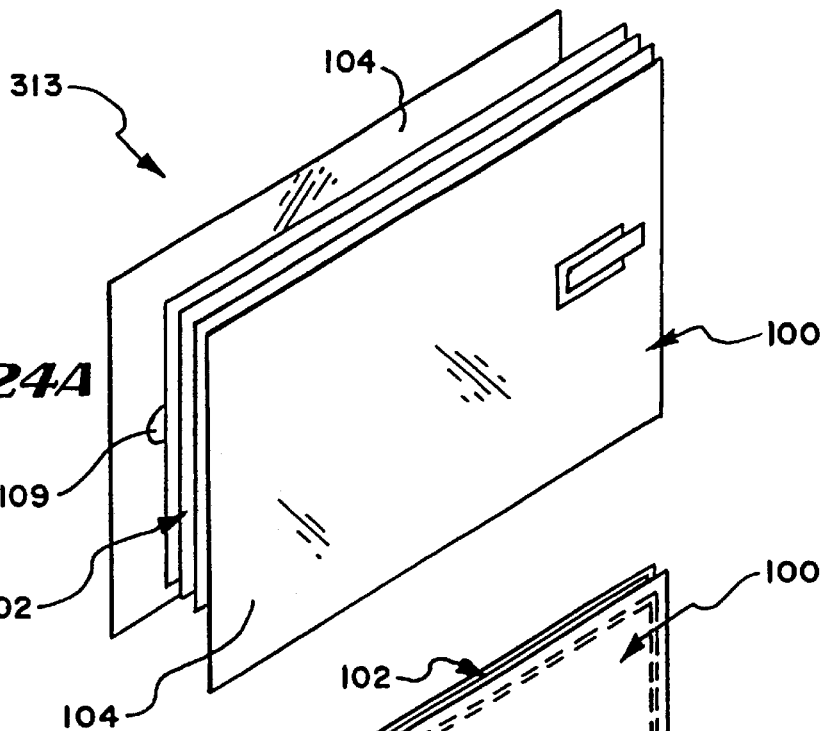
FIGS. 24A and 24B are perspective views of a leukofilter that can form a part of the fluid process circuit shown in FIGS. 3 and 23, the leukofilter comprising a filter media enclosed between two flexible sheets of plastic material, FIG. 24A showing the leukofilter in an exploded view and FIG. 24B showing the leukofilter in an assembled view.
Figure 24B:
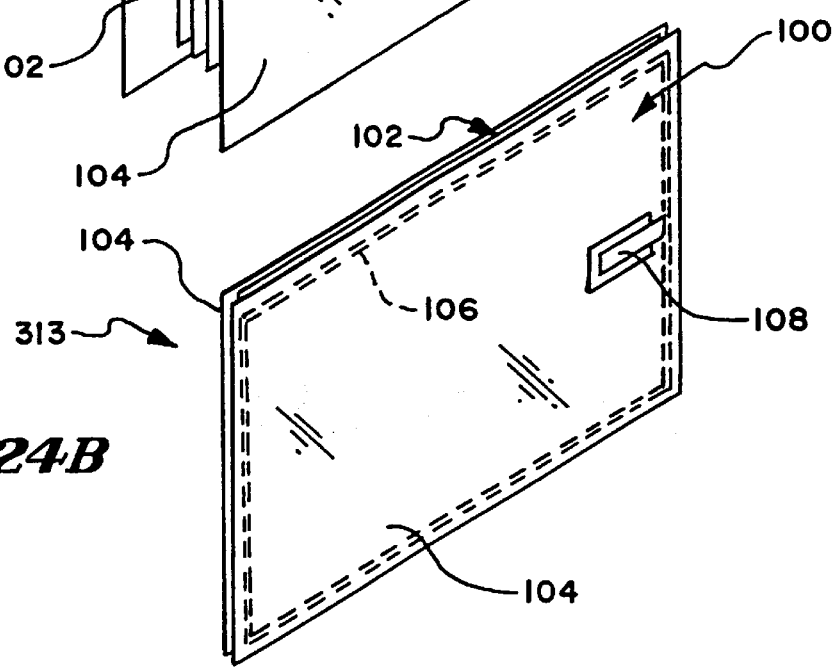

The underside of the base 388 (see FIG. 7) includes a shaped receptacle 179. The far end of the umbilicus 296 includes a shaped mount 178 (see FIGS. 24 and 24A). The mount 178 is shaped to correspond to the shape of the receptacle 179. The mount 178 can thus be plugged into the receptacle 179 (as FIG. 7 shows), to couple the umbilicus 296 in fluid communication with the channel 126.

The mount 178 is desirably made from a material that can withstand considerable flexing and twisting, to which the mount 178 can be subjected during use, e.g., Hytrel® 3078 copolyester elastomer (DuPont). The dimensions of the shaped receptacle 179 and the shaped mount 178 are preferably selected to provide a tight, dry press fit, to thereby avoid the need for solvent bonding or ultrasonic welding techniques between the mount 178 and the base 388 (which can therefore be formed from an incompatible material, such as ABS plastic).

D. The Centrifuge Assembly

Figure 10:
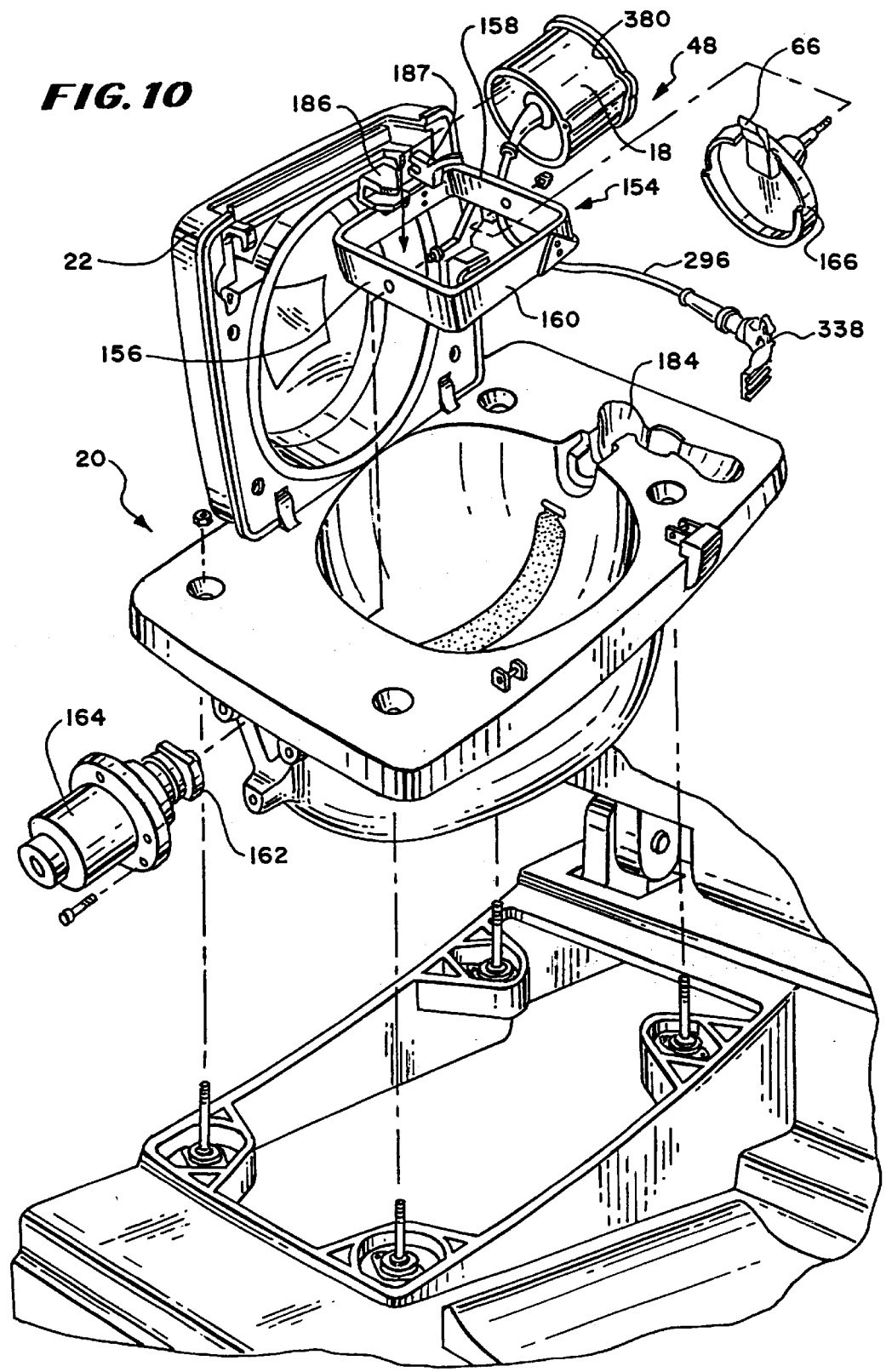
FIG. 10 is an exploded perspective view of the centrifuge station and associated centrifuge assembly of the device shown in FIGS. 1 and 2.

The centrifuge station 20 (see FIG. 10) includes a centrifuge assembly 48. The centrifuge assembly 48 is constructed to receive and support the molded processing chamber 18 and umbilicus 296 for use.

Figure 11:
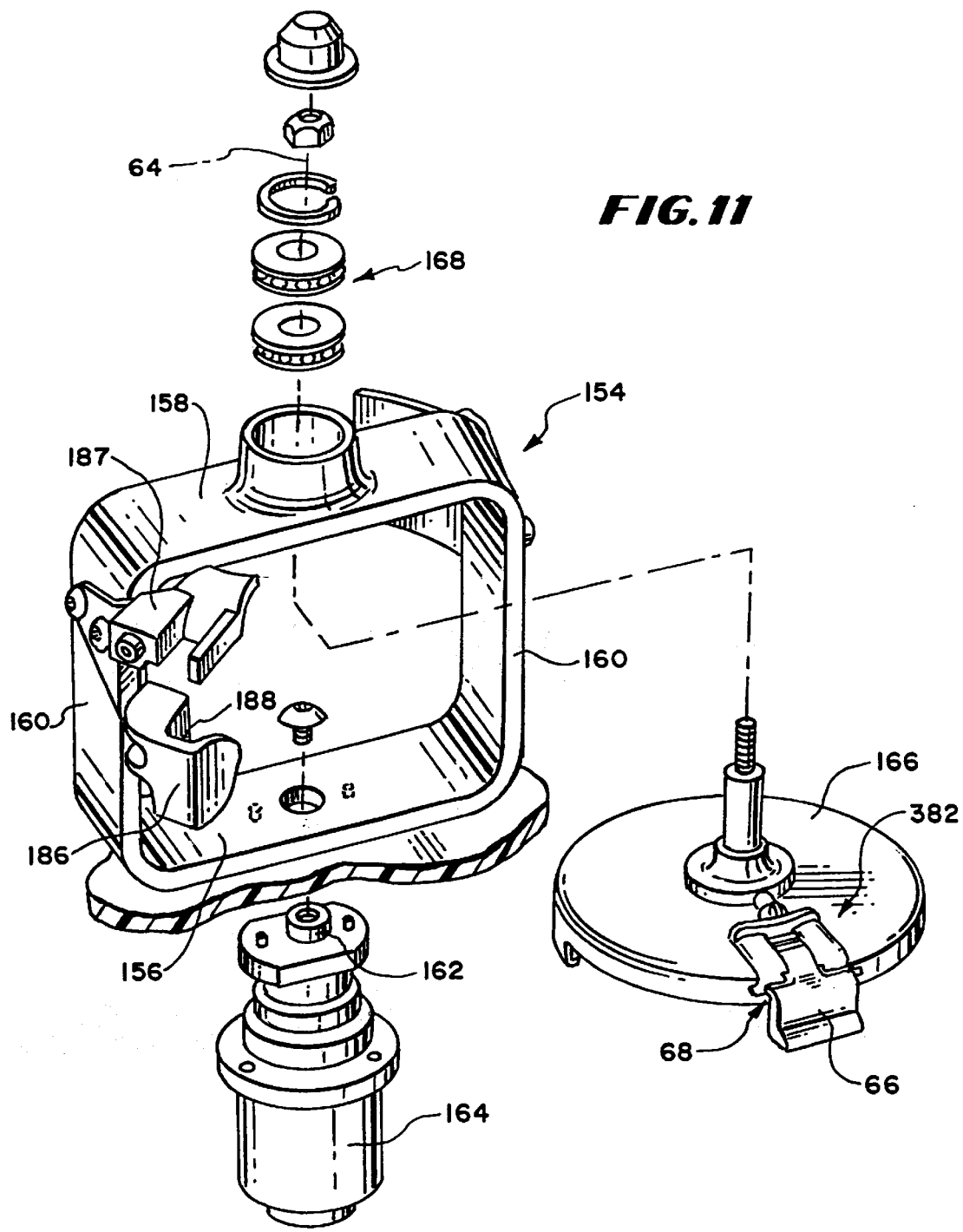
FIG. 11 is an enlarged exploded perspective view of the centrifuge assembly shown in FIG. 10.

As illustrated (see FIGS. 10 and 11), the centrifuge assembly 48 includes a yoke 154 having bottom, top, and side walls 156, 158, 160. The yoke 154 spins on a bearing element 162 (FIG. 11) attached to the bottom wall 156. An electric drive motor 164 is coupled to the bottom wall 156 of the yoke 154, to rotate the yoke 154 about an axis 64. In the illustrated embodiment, the axis 64 is essentially horizontal (see FIG. 1), although other angular orientations can be used.

A rotor plate 166 (see FIG. 11) spins within the yoke 154 about its own bearing element 168, which is attached to the top wall 158 of the yoke 154. The rotor plate 166 spins about an axis that is generally aligned with the axis of rotation 64 of the yoke 154.

As FIG. 7 best shows, the top of the processing chamber 18 includes an annular lip 380, to which the lid 150 is secured. As FIG. 12 shows, the rotor plate 166 includes a latching assembly 382 that removably grips the lip 380, to secure the processing chamber 18 on the rotor plate 166 for rotation.

The configuration of the latching assembly 382 can vary. In the illustrated embodiment (see FIGS. 13 to 15), the latching assembly 382 includes a latch arm 66 pivotally mounted on a pin in a peripheral recess 68 in the rotor plate 166. The latch arm 66 pivots between a retaining position (shown in FIGS. 13 and 14) and a releasing position (shown in FIG. 15).

In the retaining position (see FIG. 14), an annular groove 70 on the underside of the latch arm 66 engages the annular lip 380 of the processing chamber 18. The annular groove 70 on the latch arm 66 coincides with an annular groove 71 that encircles the top interior surface of the rotor plate 166. The engagement of the lip 380 within the grooves 70/71 secures the processing chamber 18 to the rotor plate 166.

In the releasing position (see FIG. 15), the annular groove 70 is swung free of engagement of the annular lip 380. This lack of engagement allows release of the processing chamber 18 from the remainder of the groove 71 in the rotor plate 166.

In the illustrated embodiment, the latching assembly 382 includes a sliding pawl 72 carried in a radial track 74 on the top of the rotor plate. In the track 74, the pawl 72 slides radially toward and away from the latch arm 66.

When the latch arm 66 is in its retaining position and the pawl 72 is located in a radial position adjacent the latch arm 66 (see FIG. 14), a finger 76 on the pawl 72 slips into and engages a cam recess 78 in the latch arm 66. The engagement between the pawl finger 76 and latch arm cam recess 78 physically resists movement of the latch arm 66 toward the releasing position, thereby locking the latch arm 66 in the retaining position.

A spring 80 within the pawl 72 normally biases the pawl 72 toward this radial position adjacent the latch arm 66, where engagement between the pawl finger 76 and latch arm cam recess 78 can occur. The latch arm 66 is thereby normally held by the pawl 72 in a locked, retaining position, to hold the processing chamber 18 during use.

The pawl 72 can be manually moved against the bias of the spring 80 radially away from its position adjacent the latch arm 66 (see FIG. 15). During this movement, the finger 76 on the pawl 72 slips free of the cam recess 78 in the latch arm 66. Free of engagement between the pawl finger 76 and latch arm cam recess 78, the latch arm 66 is unlocked and can be pivoted toward its releasing position. In the absence of manual force against the bias of the spring 80, the pawl 72 returns by spring force toward its position adjacent the latch arm 66, to lock the latch arm 66 in the chamber retaining position.

In the illustrated embodiment (see FIG. 13), the top wall 158 of the yoke 154 carries a downward depending collar 82. The collar 82 rotates in unison with the yoke 154, relative to the rotor plate 166. The collar 82 includes a sidewall 84 that is continuous, except for a cut away or open region 86.

Figure 13:
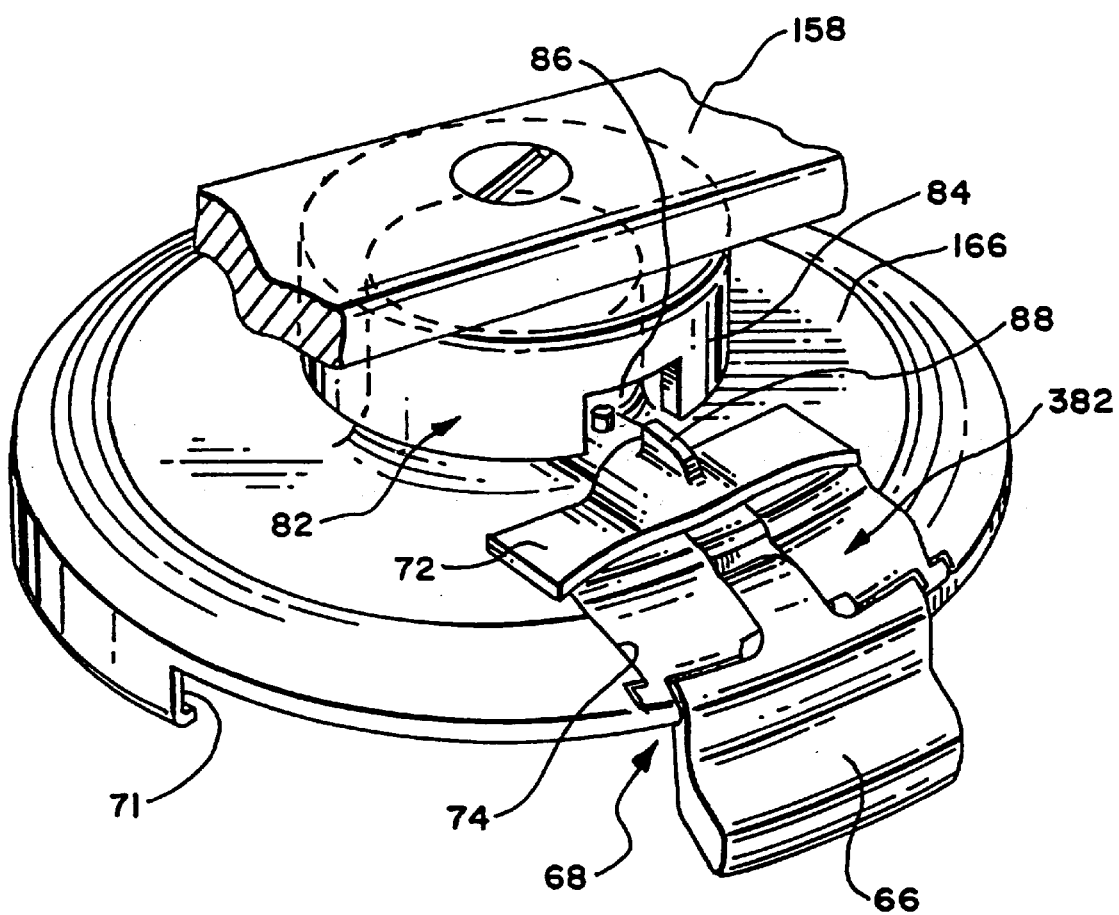
FIG. 13 is a perspective view of the rotor plate that forms a part of the centrifuge assembly shown in FIGS. 10 to 12, showing the latch assembly which releasably secures the processing chamber to the centrifuge assembly, the latch assembly being shown in its chamber retaining position.
Figure 17:
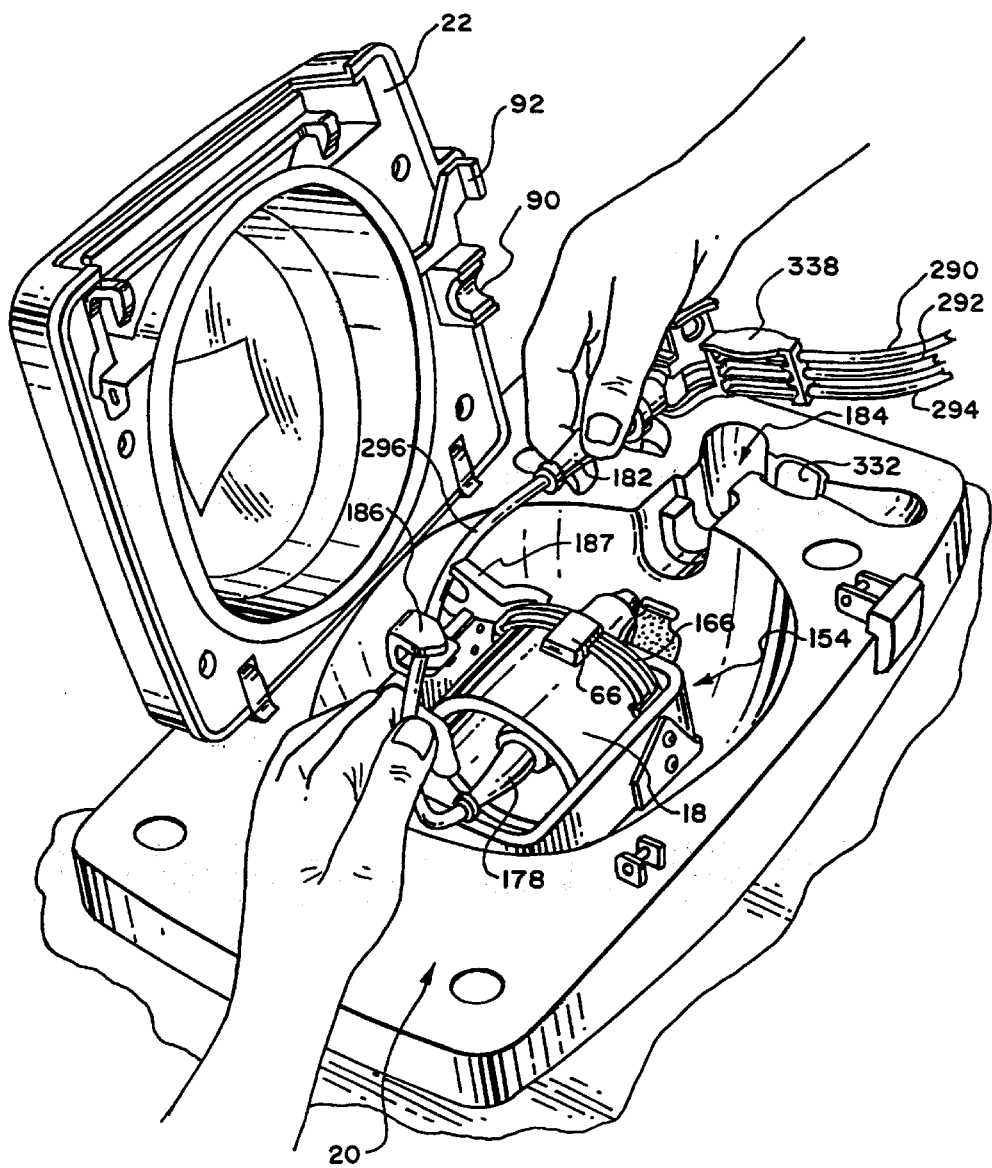

As FIG. 17 best shows, the pawl 72 includes an upstanding key element 88. The sidewall 84 of the collar 82 is located in the radial path that the key element 88 travels when the pawl 72 is manually moved against the bias of the spring 80 radially away from its position adjacent the latch arm 66. The key element 88 abuts against the collar sidewall 84, to inhibit movement of the pawl 72 in this direction, unless the open region 86 is aligned with the key element 88, as shown in FIGS. 13 and 15. The open region 86 accommodates passage of the key element 88, permitting manual movement of the pawl 72 against the bias of the spring 80 radially away from its position adjacent the latch arm 66, thereby allowing the latch arm 66 to pivot into its releasing position.

The interference between the collar sidewall 84 and the key element 88 of the pawl 72 prevents manual movement of the pawl 72 away from the latch arm 66, to unlock the latch arm 66 for movement into its releasing position, unless the open region 86 and the key element 88 register. The open region 86 is aligned on the yoke 154 so that this registration between the open region 86 and the key element 88 occurs only when the rotor plate 166 is in a prescribed rotational position relative to the yoke 154. In this position (see FIG. 12), the sidewalls 160 of the yoke 154 are located generally parallel to the plane of the opening to the compartment, providing open access to the interior of the yoke 154. In this position (see FIG. 16), the processing chamber 18 can be freely placed without interference into the interior of the yoke 154, and loaded onto the rotor plate 166. In this position, uninhibited manual movement of the pawl 72 allows the operator to pivot the latch arm 66 into its releasing position, to bring the lid 150 of the chamber 18 into contact against the rotor plate 166. Subsequent release of the pawl 72 returns the pawl 72 toward the latch arm 66 and allows the operator to lock the latch arm 66 in its retaining position about the lip 380 of the chamber 18. The reverse sequence is accommodated when it is time to remove the processing chamber 18 from the rotor plate 166.

Figure 16:
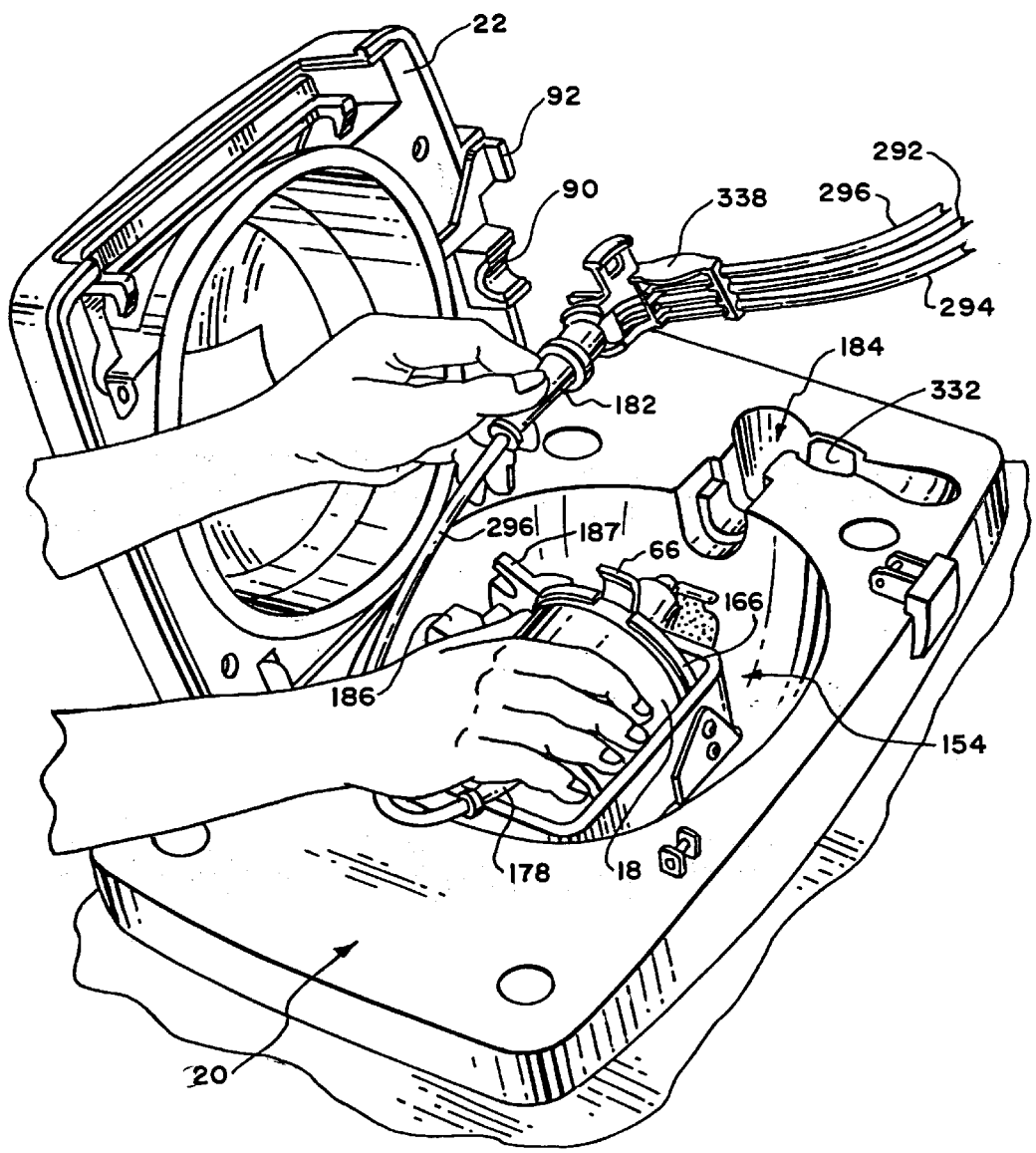
FIGS. 16 to 18 are a series of perspective view of the centrifuge station of the device shown in FIGS. 1 and 2, showing the sequence of loading the processing chamber and associated umbilicus on the centrifuge assembly prior to use.

This arrangement makes possible a straightforward sequence of acts to load the processing chamber 18 for use and to unload the processing chamber 18 after use (see FIG. 16). As FIGS. 17 and 18 further show, easy loading of the umbilicus 296 is also made possible in tandem with fitting the processing chamber 18 to the rotor plate 166.

A sheath 182 on the near end of the umbilicus 296 fits into a preformed, recessed pocket 184 in the centrifuge station 20. The pocket 184 holds the near end of the umbilicus 296 in a non-rotating stationary position aligned with the mutually aligned rotational axes 64 of the yoke 154 and rotor plate 166.

The preformed pocket 184 is also shaped to accommodate loading of the fixture 338 at the same time the sheath 182 is inserted. The tubes 290, 292, and 294 are thereby placed and removed as a group in association with the sensing station 332, which is located within the pocket 184.

Umbilicus support members 186 and 187 (see FIG. 12) are carried by a side wall 160 of the yoke 154. When the rotor plate 166 is located in its prescribed rotational position to enable easy loading of the chamber 18 (see FIGS. 17 and 18), the support members 186 and 187 are presented on the left side of the processing chamber 18 to receive the umbilicus 296 at the same time that the sheath 182 and fixture 338 are manipulated for fitting into the pocket 184.

Figure 19:
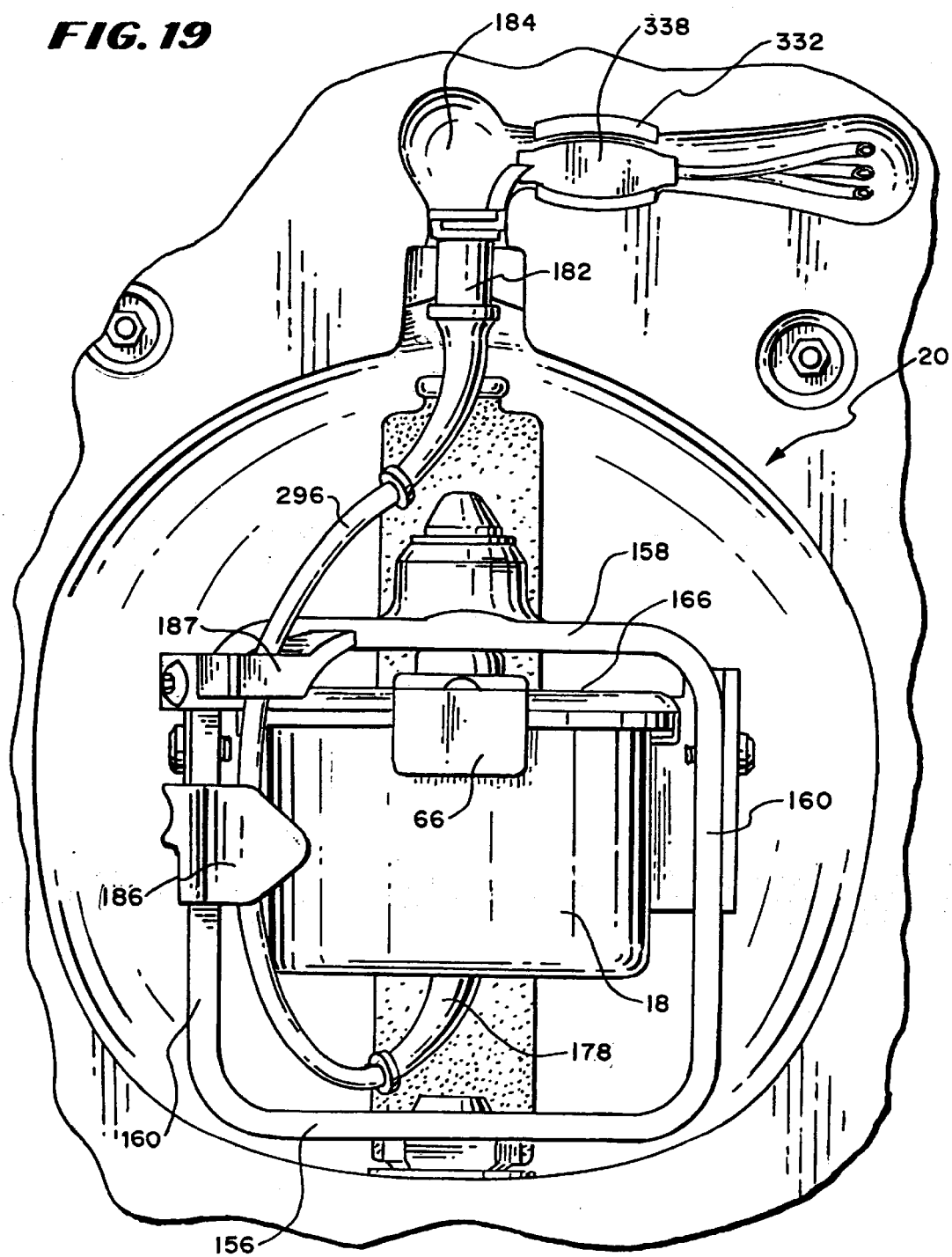
FIGS. 19 to 22 are a series of perspective view of the centrifuge station of the device shown in FIGS. 1 and 2, after loading the processing chamber and associated umbilicus on the centrifuge assembly, showing at ninety degree intervals the travel of the umbilicus to impart rotation to the processing chamber, as driven and restrained by umbilicus support members carried by the yoke.
Figure 20:
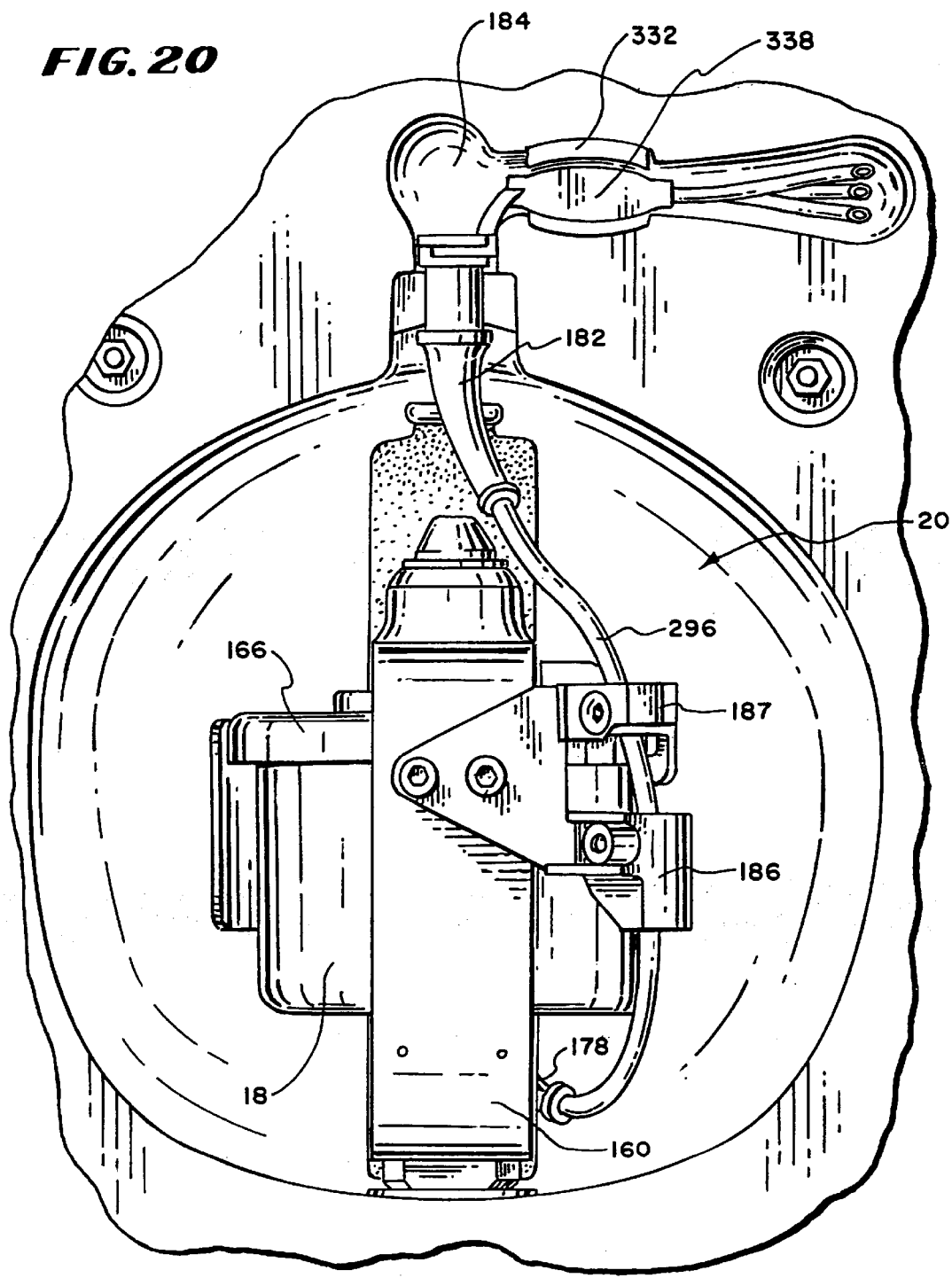
Figure 21:
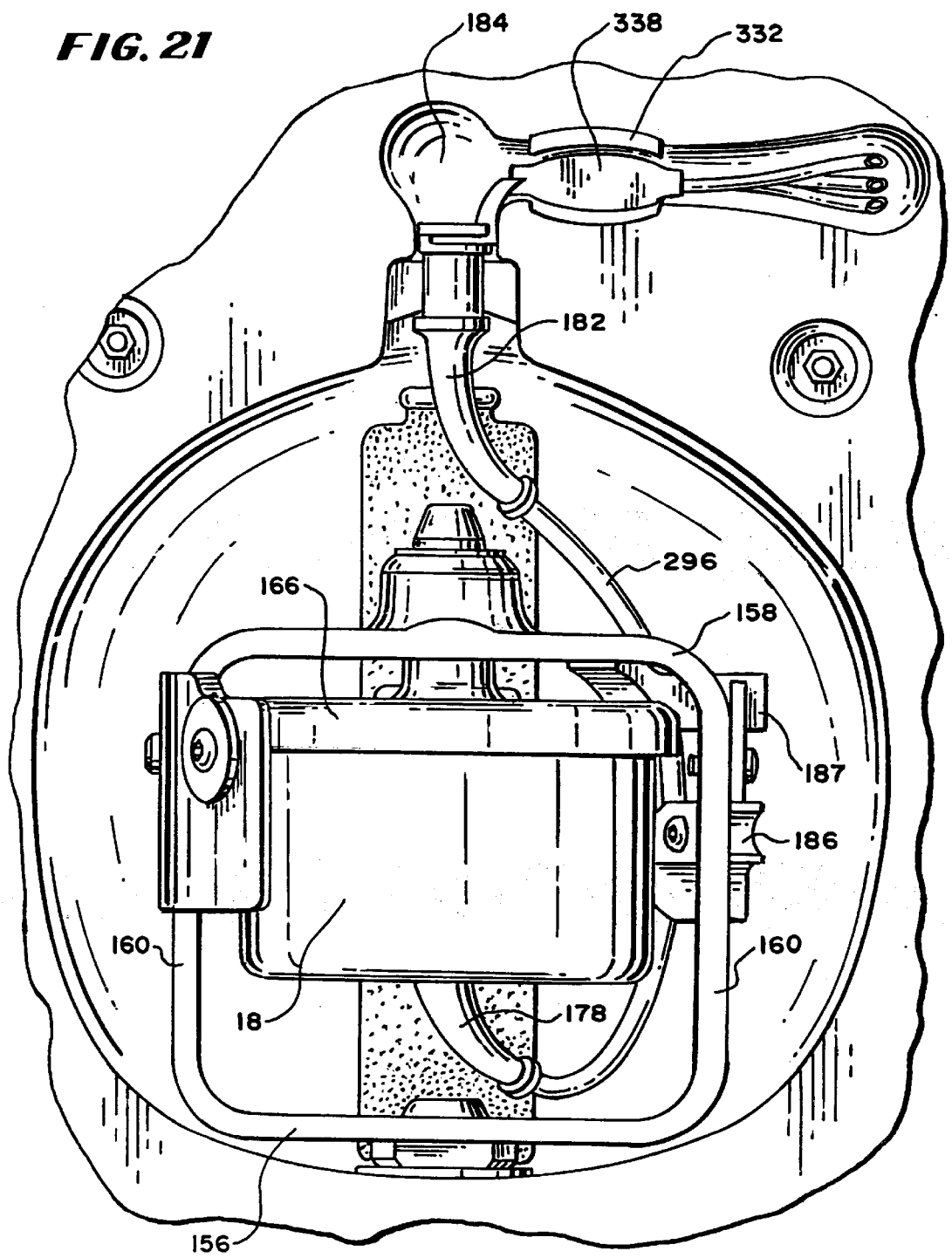
Figure 22:
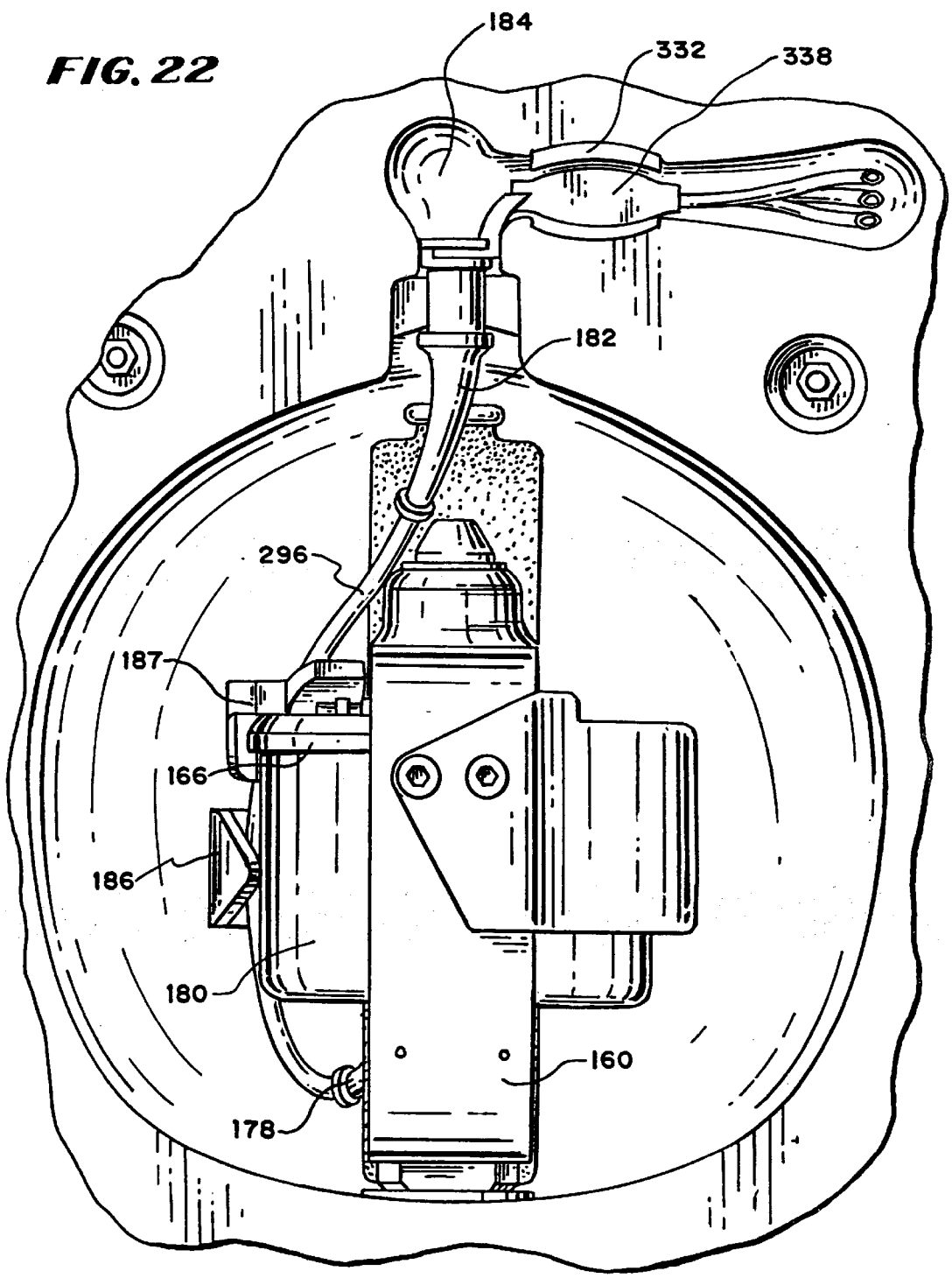

As FIG. 19 shows, one member 186 receives the mid portion of the umbilicus 296. The member 186 includes a surface 188 against which the mid portion of the umbilicus 296 rests. The surface 188 forms a channel that extends generally parallel to the rotational axis 64 and that accommodates passage of the mid portion of the umbilicus 296. The surface 188 inhibits travel of the mid portion of the umbilicus 296 in radial directions toward and away from the rotational axis 64. However, the surface 188 permits rotation or twisting of the umbilicus 296 about its own axis.

The other member 187 receives the upper portion of the umbilicus 296. The member 187 includes a surface 190 against which the upper portion of the umbilicus 296 rests. The surface 190 forms a channel inclined toward the top wall 158 of the yoke 154. The surface 190 guides the upper portion of the umbilicus 296 toward the recessed pocket 184, which is located axially above the top wall 158 of the yoke 154, where the umbilicus sheath 182 and fixture 338 are fitted. Like the surface 188, the surface 190 inhibits travel of the upper portion of the umbilicus 296 in radial directions toward and away from the rotational axis 64. However, like the surface 188, the surface 190 permits rotation or twisting of the umbilicus 296 about its own axis.

Figure 18:
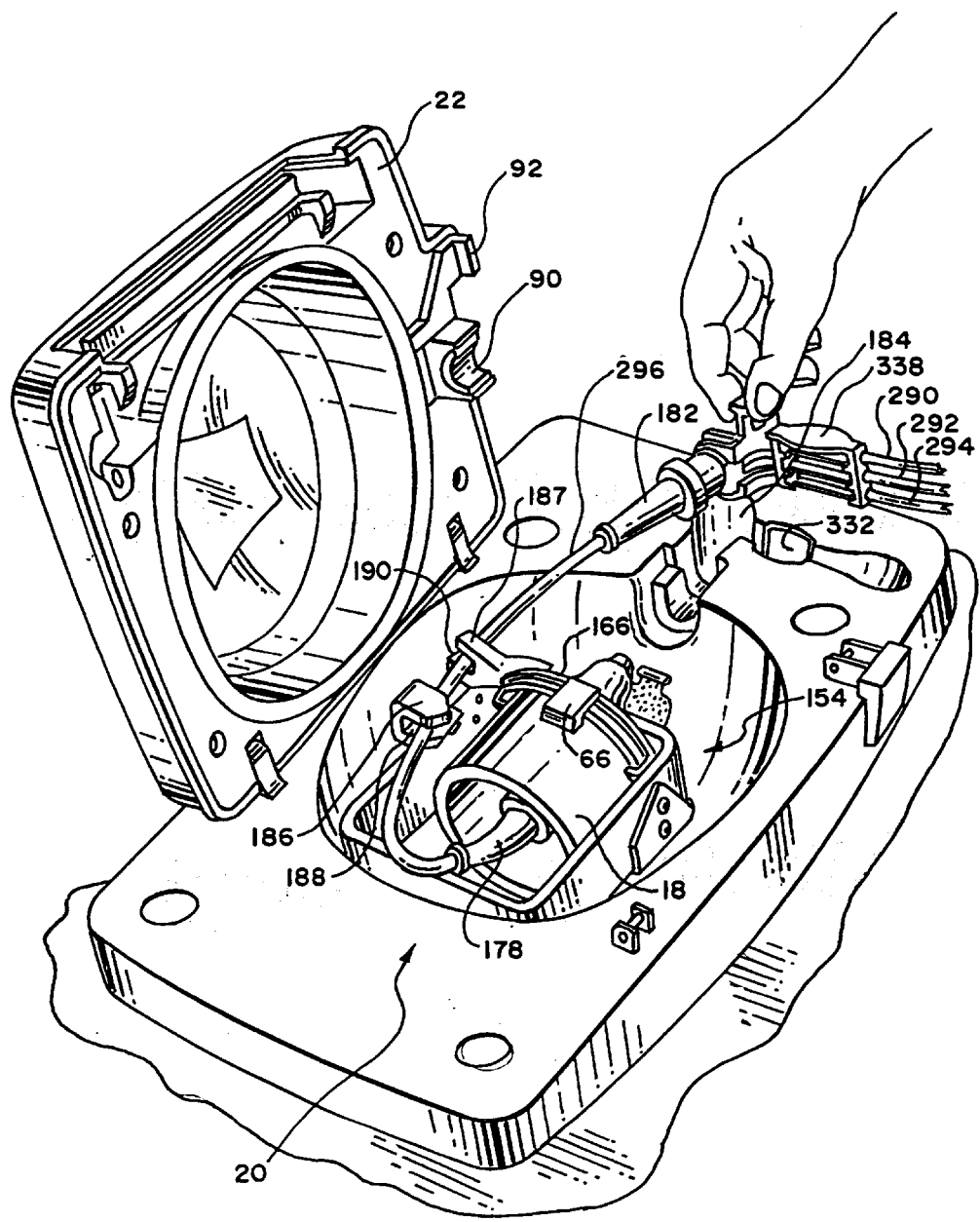

Closing the centrifuge station door 20 positions a holding bracket 90 on the underside of the door 20 in registry with the sheath 182 (see FIGS. 17 and 18). Another holding bracket 92 on the underside of the door 20 is positioned in registry with the fixture 338 when the door 20 is closed. A releasable latch 94 preferably holds the door shut during operation of the centrifuge assembly 48.

During operation of the centrifuge assembly 48 (see FIGS. 19 to 22), the support members 186 and 187 carry the umbilicus 296 so that rotation of the yoke 154 also rotates the umbilicus 296 in tandem about the yoke axis. Constrained within the pocket 184 at its near end (i.e., at the sheath 182) and coupled to the chamber 16 at its far end (i.e., by the mount 178), the umbilicus 296 twists upon the surfaces 188 and 190 about its own axis as it rotates about the yoke axis 64, even as the surfaces 188 and 190 inhibit radial travel of the umbilicus relative to the rotation axis 64. The twirling of the umbilicus 296 about its axis as it rotates upon the surfaces 188 and 190 at one omega with the yoke 154 (typically at a speed of about 2250 RPM) imparts a two omega rotation to the processing chamber 18 secured for rotation on the rotor plate 166.

The relative rotation of the yoke 154 at a one omega rotational speed and the rotor plate 166 at a two omega rotational speed, keeps the umbilicus 296 untwisted, avoiding the need for rotating seals. The illustrated arrangement also allows a single drive motor 164 to impart rotation, through the umbilicus 296, to the mutually rotating yoke 154 and processing chamber 18 carried on the rotor plate 166. Further details of this arrangement are disclosed in Brown et al U.S. Pat. No. 4,120,449, which is incorporated herein by reference.

The umbilicus 296 can stretch in response to the rotational forces it encounters. The dimensions of a given umbilicus 296 are also subject to normal manufacturing tolerances. These factors affect the flight radius of the umbilicus 296 during use; as well as the stress encountered by the mount 178 at the far end of the umbilicus 296, which serves as the two omega torque transmitter to drive the processing chamber 18; as well as the lateral loads acting on the centrifuge and motor bearings.

As FIGS. 19 to 22 show, the support members 186 and 187 on the yoke serve to physically confine the flight of the umbilicus 296 between the one omega region (mid portion) and two omega region (far end portion), as well as between the one omega region (mid portion) and zero omega region (near end portion) of the umbilicus 296. By confining the umbilicus 296 to a predefined radial distance from and radial orientation with respect to the rotational axis of the centrifuge assembly 48, the support members 186 and 187 serve to attenuate the factors that can affect umbilicus performance and endurance.

The support members 186 and 187 make possible a bearing-less umbilicus assembly with no moving parts, while leading to reduced stress at the two omega torque region, where stresses tend to be greatest. The surfaces 188 and 190 of the support members 186 and 187 can be formed and oriented to accommodate rotation of the umbilicus 296 and the driving of the processing chamber 18 in either clockwise or counterclockwise directions.

In the illustrated embodiment, the surfaces 188 and 190 of the support members 186 and 187 are preferably fabricated from a low friction material, to thereby eliminate the need for external lubrication or rotating bearings on the umbilicus 296 itself. The material used can, e.g., comprise Teflon® polytetrafluoroethylene material (DuPont) or an ultra high molecular weight polyethylene. Made from such materials, the surfaces 188 and 190 minimize umbilicus drive friction and the presence of particulate matter due to umbilicus wear.

In a representative embodiment (see FIG. 4), the umbilicus 296 desirably comprises a two layer co-extruded assembly. The interior or core layer 96 desirably comprises Hytrel® 4056 copolyester elastomer (DuPont). The outside layer 98 desirably comprises Hytrel® 3078 copolyester elastomer (DuPont). The outside layer 98 may comprise a relatively thin extrusion, compared to the core layer 96.

In this arrangement, the outside layer 98 of Hytrel® 3078 copolyester elastomer serves as a compatible interface to accommodate over-molding of the zero omega sheath 182 and the two omega mount 178, which may comprise the same Hytrel® 3078 material or an otherwise compatible material. Absent material compatibility, solvents (e.g., methylene chloride) or other forms of surface treatment may be required to facilitate a robust bond between these elements and the umbilicus. Hytrel® 3078 material is desired for the sheath 182, and the mount 178 because it can withstand considerable flexing and twisting forces, to which these regions of the umbilicus are subjected during use.

The core layer 96 of Hytrel® 4056 copolyester elastomer can be readily solvent bonded to conventional flexible medical grade polyvinyl tubing, from which the tubes 290, 292, and 294 are desirably made.

II. Double Red Blood Cell Collection Procedure

Use of the set 12 in association with the device 14 and controller 16 to conduct a typical double unit red blood cell collection procedure will now be described for illustrative purposes.

A. The Cassette

Figure 23:
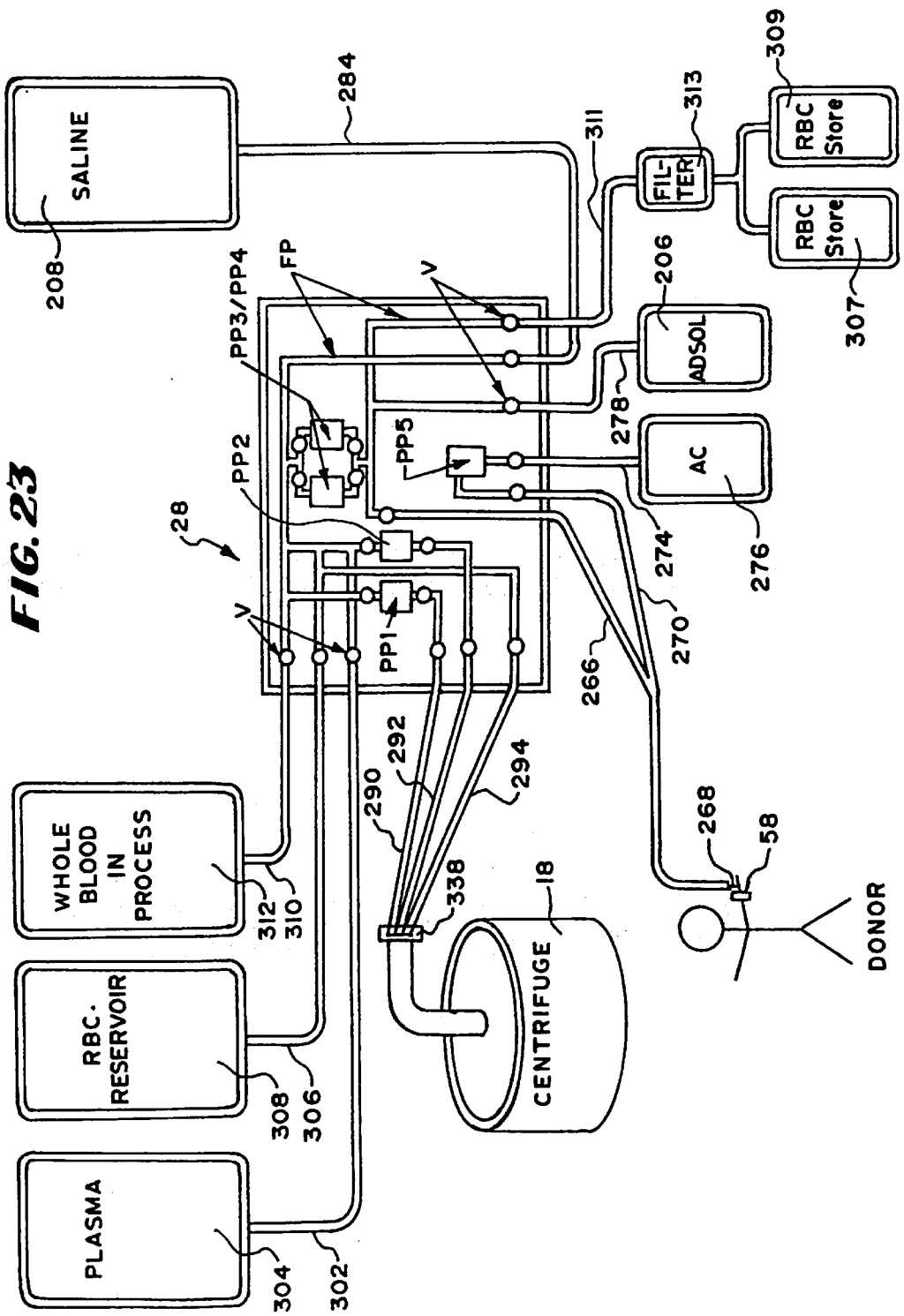
FIG. 23 is a schematic view of a fluid processing circuit of the type shown in FIG. 3, showing certain details of the arrangement of pumps that convey blood and fluid through the circuit.

The cassette 28 used for a procedure of this type desirably includes dual pneumatic pump chambers PP3 and PP4 (see FIG. 23) which are operated by the controller 16 in tandem to serve as a general purpose, donor interface pump. The dual donor interface pump chambers PP3 and PP4 work in parallel. One pump chamber draws fluid, while the other pump chamber expels fluid. The dual pump chambers PP3 and PP4 thereby alternate draw and expel functions to provide a uniform outlet flow.

The cassette 28 also desirably includes a pneumatic pump chamber PP5, which serves as a dedicated anticoagulant pump, to draw anticoagulant from the container 276 and meter the anticoagulant into the blood drawn from the donor.

The cassette 28 also desirably includes a pneumatic pump chamber PP1 that serves as a dedicated in-process whole blood pump, to convey whole blood from the reservoir 312 into the processing chamber 18. The dedicated function of the pump chamber PP1 frees the donor interface pump chambers PP3 and PP4 from the added function of supplying whole blood to the processing chamber 18. Thus, the in-process whole blood pump chamber PP1 can maintain a continuous supply of blood to the processing chamber 18, while the donor interface pump chambers PP3 and PP4 operate in tandem to simultaneously draw and return blood to the donor through the single phlebotomy needle. Processing time is thereby minimized.

The cassette 28 also desirably includes a pneumatic pump chamber PP2 that serves as a plasma pump, to convey plasma from the processing chamber 18. The ability to dedicate separate pumping functions provides a continuous flow of blood into and out of the processing chamber 18, as well as to and from the donor.

B. Capacitive Flow Sensing

The controller 16 desirably includes means for monitoring fluid flow through the pump chambers PP1 to PP5. In the illustrated embodiment, the pump and valve station 30 carries electrode circuits 206 associated with each pump chamber PP1 to PP5. The electrode circuits 206 can be located, e.g., within the pneumatic actuator ports 204 in the pump and valve station 30 (see FIG. 29) that apply negative and positive pressure to the diaphragms to thereby draw fluid into the chambers PP1 to PP5 and expel fluid from the chambers PP1 to PP5. The electrode circuits 206 are coupled to an electrical source and are in electrical conductive contact with fluids within their respective pump chambers PP1 and PP5.

The passage of electrical energy through each electrode circuit 206 creates an electrical field within the respective pump chamber PP1 to PP5. Cyclic deflection of the diaphragm associated with a given pump chamber to draw fluid into and expel fluid from the pump chamber PP1 to PP5 changes the electrical field, resulting in a change in total capacitance of the circuit through the electrode. Capacitance increases as fluid is draw into the pump chamber PP1 to PP5, and capacitance decreases as fluid is expelled from pump chamber PP1 to PP5.

In the arrangement, the electrode circuits 206 each includes a capacitive sensor (e.g., a Qprox E2S). The capacitive sensor registers changes in capacitance for the electrode circuit 206 for each pump chamber PP1 to PP5. The capacitance signal for a given electrode circuit 206 has a high signal magnitude when the pump chamber is filled with liquid, has a low signal magnitude signal when the pump chamber is empty of fluid, and has a range of intermediate signal magnitudes when the diaphragm occupies intermediate positions.

At the outset of a blood processing procedure, the controller 16 can calibrate the difference between the high and low signal magnitudes for each sensor to the maximum stroke volume of the respective pump chamber. The controller 16 can then relate the difference between sensed maximum and minimum signal values during subsequent draw and expel cycles to fluid volume drawn and expelled through the pump chamber. The controller 16 can sum the fluid volumes pumped over a sample time period to yield an actual flow rate.

The controller 16 can compare the actual flow rate to a desired flow rate. If a deviance exists, the controller 16 can vary pneumatic pressure pulses delivered to the actuators for the pump chambers PP1 to PP5 to minimize the deviance.

The controller 16 can also operate to detect abnormal operating conditions based upon the variations in the electric field and to generate corresponding alarm outputs. The controller 16 can, e.g., monitor for an increase in the magnitude of the low signal magnitude over time. The increase in magnitude reflects the presence of air inside a pump chamber.

For example, the controller 16 can generate a derivative of the signal output of the sensor 426. Changes in the derivative, or the absence of a derivative, reflects a partial or complete occlusion of flow through the pump chamber PP1 to PP5. The derivative itself also varies in a distinct fashion depending upon whether the occlusion occurs at the inlet or outlet of the pump chamber PP1 to PP5.

1. Monitoring Vein Flow Conditions

By using capacitive sensing and by also counting pump strokes (i.e., the application of negative pressure upon the diaphragm of a given pump chamber to draw fluid into the chamber), the controller 16 can also monitor vein flow conditions, and, in particular, assess and respond to real or potential vein occlusion conditions.

When blood is pumped from the donor, the donor's vein may show difficulties in keeping up with the commanded draw rate that operation of the donor pump chambers PP3/PP4 imposes. In the case of restricted blood flow from the donor, the donor pumps PP3 and PP4 do not fill properly in response to the commanded sequence of pump strokes. The controller 16 attempts to assess and mediate blood supply interruptions due to vein problems before generating a vein occlusion alarm, which suspends processing.

For example, the controller 16 can count the number of consecutive attempted pump strokes for which no blood flow into the pump chambers PP3 and PP4 occurs (which blood flow or absence of blood flow can be detected by capacitive sensing, as above described). A potential donor draw occlusion condition can be deemed to occur when a prescribed number (e.g., 3) of consecutive incomplete fill donor pump strokes takes place.

When a potential donor draw occlusion condition is detected, the controller 16 attempts to rectify the condition by increasing pressure of the pressure cuff 58 and/or decreasing the commanded draw rate, before generating a processing-halting vein occlusion alarm.

More particularly, in a representative implementation, when a donor draw occlusion condition is detected, the controller 16 executes a potential draw occlusion condition function (in shorthand, the "Potential Occlusion Function"). The Potential Occlusion Function first suspends the draw for a period of time (e.g. upwards to 20 seconds, and desirably about 10 seconds) to rest the vein. While the vein rests, the controller 16 also increases the pressure cuff pressure by a preset increment (e.g., upwards to 25 mmHg, and desirably about 10 mmHg), unless cuff pressure, when adjusted, exceeds a prescribed maximum (e.g., upwards to 100 mmHg, desirably about 70 mmHg). If the prescribed maximum cuff pressure condition exists, no incremental changes to the cuff pressure are made during the prescribed vein rest interval.

After the prescribed vein rest interval, the Potential Occlusion Function resets the attempted pump stroke counter to zero and resumes the draw cycle. The controller 16 monitors the initial series of consecutive pump strokes during the resumed draw cycle, up to a first threshold number of pump strokes (e.g., 5). The magnitude of the first threshold number is larger that the number of consecutive incomplete fill donor pump strokes (i.e., 3) that indicate a potential donor draw occlusion condition. The magnitude of the first threshold number is selected to accurate assess, after a potential donor draw occlusion condition arises, whether a true donor draw occlusion exists. In the illustrated embodiment, if within the first five pump strokes (or whatever the first threshold number is), three consecutive incomplete fill donor pump strokes take place, the controller 16 assumes that a true donor draw occlusion exists, and thus generates an occlusion alarm. With the generation of an occlusion alarm, the controller 16 suspends processing, until the operator can establish that it is safe to resume.

If within the first threshold number of pump strokes, three consecutive incomplete fill donor pump strokes do not take place, the controller 16 assumes that a true vein occlusion may not exist, and that the potential occluded flow condition was either transient, or at least capable of correction short of suspending the procedure. In this event, the Potential Occlusion Function allows the resumed draw cycle to continue beyond the first threshold number of pump strokes up to a second threshold number of pump strokes (e.g., 20 to 100, and desirable about 50).

If at any time between the first threshold number of pump strokes and the second threshold number of pump strokes, three consecutive incomplete fill donor pump strokes take place, the Potential Occlusion Function institutes another vein rest interval (e.g. upwards to 20 seconds, and desirably about 10 seconds). While the vein rests, the Potential Occlusion Function also again increases the pressure cuff pressure by a preset increment (e.g., upwards to 25 mmHg, and desirably about 10 mmHg). While the vein rests, the Potential Occlusion Function also lowers the draw rate by a preset decrement (e.g., upwards to 20 ml/min, and desirably about 10 ml/min). If the draw rate, when lowered, is less than a prescribed minimum draw rate (e.g., 70 to 90 ml/min), the controller 16 generates an occlusion alarm. Otherwise, the Potential Occlusion Function resets the attempted pump stroke counter to zero, and resumes the draw cycle at the increased cuff pressure and decreased draw rate.

The controller 16 again monitors the initial series of consecutive pump strokes during the resumed draw cycle, up to the first threshold number of pump strokes (e.g., 5). If within the first threshold number of pump strokes, three consecutive incomplete fill donor pump strokes take place, the controller 16 assumes that a true donor draw occlusion exists, and thus generates an occlusion alarm and also suspends processing.

However, if within the first threshold number of pump strokes, three consecutive incomplete fill donor pump strokes do not take place, the controller 16 allows the resumed draw cycle to continue beyond the first threshold number of pump strokes up to the second threshold number of pump strokes (e.g., 20 to 100, and desirable about 50). If at any time between the first threshold number of pump strokes and the second threshold number of pump strokes, three consecutive incomplete fill donor pump strokes take place, the Potential Occlusion Function again institutes another vein rest interval (e.g. upwards to 20 seconds, and desirably about 10 seconds). While the vein rests, the Potential Occlusion Function also again increases the pressure cuff pressure by a preset increment (e.g., upwards to 25 mmHg, and desirably about 10 mmHg). While the vein rests, the Potential Occlusion Function also again lowers the draw rate by a preset decrement (e.g., upwards to 20 ml/min, and desirably about 10 ml/min), unless the draw rate, when lowered, is less than a prescribed minimum draw rate (e.g., 70 to 90 ml/min), in which case the controller 16 generates an occlusion alarm. Otherwise, the Potential Occlusion Function resets the attempted pump stroke counter to zero, and resumes the draw cycle at the increased cuff pressure and decreased draw rate.

The controller 16 continues to repeat the steps of the Potential Occlusion Function, using the first and second pump stroke number thresholds to gage whether a true vein occlusion exists, and either generating an occlusion alarm if it does, or continuing to attempt remedial action (by increasing cuff pressure and/or decreasing draw rate), or cancelling the potential donor draw occlusion condition when three consecutive incomplete fill donor pump strokes are not observed during either the first or second threshold periods following a potential donor occlusion condition.

If no three consecutive incomplete fill donor pump strokes take place within the second threshold number of strokes following a potential donor draw occlusion condition, the controller 16 assumes that a true vein occlusion does not exist. The draw cycle continues, and the controller 16 continues to count pump strokes. If the prescribed number (e.g., 3) of consecutive incomplete fill donor pump strokes subsequently takes place, the controller 16 assumes that this event is unrelated to any previous occlusion event condition, and generates a new potential donor draw occlusion condition, executing the Potential Occlusion Function from the start.

It should be appreciated that the Potential Occlusion Function, as just described, can be used with any blood processing device that has means for detecting when a draw blood pumping command does not result in blood flow through the pump.

C. Blood Processing Cycles

Prior to undertaking the double unit red blood cell collection procedure, as well as any blood collection procedure, the controller 16 conducts an appropriate integrity check of the cassette 28, to determine whether there are any leaks in the cassette 28. Once the cassette integrity check is complete and no leaks are found, the controller 16 begins the desired blood collection procedure.

In general, using the processing chamber shown in FIG. 9), whole blood is introduced into and separated within the processing chamber 18 as it rotates. As the processing chamber 18 rotates (arrow R in FIG. 9), the umbilicus 296 conveys whole blood into the channel 126 through the passage 146. The whole blood flows in the channel 126 in the same direction as rotation (which is counterclockwise in FIG. 9). Alternatively, the chamber 18 can be rotated in a direction opposite to the circumferential flow of whole blood, i.e., clockwise, but rotation in the same direction as circumferential blood flow is preferred.

The whole blood separates as a result of centrifugal forces. Red blood cells are driven toward the high-G wall 124, while lighter plasma constituent is displaced toward the low-G wall 122. In this flow pattern, a dam 384 projects into the channel 126 toward the high-G wall 124. The dam 384 prevents passage of plasma, while allowing passage of red blood cells into a channel 386 recessed in the high-G wall 124. The channel 386 directs the red blood cells into the umbilicus 296 through the radial passage 144. The plasma constituent is conveyed from the channel 126 through the radial passage 142 into umbilicus 296.

1. Collection Cycle

During a typical collection cycle of the double unit red blood cell collection procedure, whole blood drawn from the donor is processed to collect two units of red blood cells, while returning plasma to the donor. The donor interface pumps PP3/PP4 in the cassette, the anticoagulant pump P5 in the cassette, the in-process pump PP1 in the cassette, and the plasma pump PP2 in the cassette are pneumatically driven by the controller 16, in conjunction with associated pneumatic valves, to draw anticoagulated blood into the in-process container 312, while conveying the blood from the in-process container 312 into the processing chamber 18 for separation. This arrangement also removes plasma from the processing chamber into the plasma container 304, while removing red blood cells from the processing chamber into the red blood cell container 308. This phase continues until an incremental volume of plasma is collected in the plasma collection container 304 (as monitored by a weigh sensor) or until a targeted volume of red blood cells is collected in the red blood cell collection container (as monitored by a weigh sensor).

If the volume of whole blood in the in-process container 312 reaches a predetermined maximum threshold before the targeted volume of either plasma or red blood cells is collected, the controller 16 terminates operation of the donor interface pumps PP3/PP4 to terminate collection of whole blood in the in-process container 312, while still continuing blood separation. If the volume of whole blood reaches a predetermined minimum threshold in the in-process container 312 during blood separation, but before the targeted volume of either plasma or red blood cells is collected, the controller 16 returns to drawing whole blood to thereby allow whole blood to enter the in-process container 312. The controller toggles between these two conditions according to the high and low volume thresholds for the in-process container 312, until the requisite volume of plasma has been collected, or until the target volume of red blood cells has been collected, whichever occurs first.

2. Return Cycle

During a typical return cycle (when the targeted volume of red blood cells has not been collected), the controller 16 operates the donor interface pumps PP3/PP4 within the cassette 28, the in-process pump PP1 within the cassette, and the plasma pump PP2 within the cassette, in conjunction with associated pneumatic valves, to convey anticoagulated whole blood from the in-process container 312 into the processing chamber 18 for separation, while removing plasma into the plasma container 304 and red blood cells into the red blood cell container 308. This arrangement also conveys plasma from the plasma container 304 to the donor, while also mixing saline from the container 288 in line with the returned plasma. The in line mixing of saline with plasma raises the saline temperature and improves donor comfort. This phase continues until the plasma container 304 is empty, as monitored by the weigh sensor.

If the volume of whole blood in the in-process container 312 reaches a specified low threshold before the plasma container 304 empties, the controller 16 terminates operation of the in-process pump PP1 to terminate blood separation. The phase continues until the plasma container 304 empties.

Upon emptying the plasma container 304, the controller 16 conducts another collection cycle. The controller 16 operates in successive collection and return cycles until the weigh sensor indicates that a desired volume of red blood cells have been collected in the red blood cell collection container 308. The controller 16 terminates the supply and removal of blood to and from the processing chamber, while operating the donor interface pumps PP3/PP4 in the cassette 28 to convey plasma remaining in the plasma container 304 to the donor. The controller 16 next operates the donor interface pumps PP3/PP4 in the cassette to convey the blood contents remaining in the in-process container 312 to the donor as well as convey saline to the donor, until a prescribed replacement volume amount is infused, as monitored by a weigh sensor.

3. In-Line Leukofiltration Cycle

When the collection of red blood cells and the return of plasma and residual blood components has been completed, the controller 16 switches, either automatically or after prompting the operator, to an in-line leukofiltration cycle. During this cycle, red blood cells are removed from the red blood cell collection reservoir 308 and conveyed into the red blood cell storage containers 307 and 308 through the leukocyte removal filter 313. At the same time, a desired volume of red blood cell storage solution from the container 208 is mixed with the red blood cells.

In the first stage of this cycle, the controller 16 operates donor interface pumps PP3/PP4 in the cassette to draw air from the red blood cell storage containers 307 and 309, the filter 313, and the line 311, and to transfer this air into the red blood cell collection reservoir 308. This stage minimizes the volume of air residing in the red blood cell storage containers 307 and 309 before the leukocyte removal process begins. The stage also provides a volume of air in the red blood cell collection container 308 that can be used purge red blood cells from the filter 313 into the red blood cell collection containers 307 and 309 once the leukocyte removal process is completed.

In the next stage, the controller 16 operates the donor interface pumps PP3/PP4 in the cassette 28 to draw a priming volume of storage solution from the solution container 208 into the red blood cell collection reservoir 308. This stage primes the tubing 278 between the container 208 and the cassette 28, to minimize the volume of air pumped into the final red blood cell storage containers 307 and 309.

In the next stage, the controller 16 operates the donor interface pumps PP3/PP4 in the cassette 28 to alternate pumping red blood cells from the red blood cell collection reservoir 308 into the red blood cell collection containers 307 and 309 (through the filter 313), with pumping of red blood cell storage solution from the container 208 into the red blood cell collection containers 307 and 309 (also through the filter 313). This alternating process mixes the storage solution with the red blood cells. The controller 16 counts the pneumatic pump strokes for red blood cells and the storage solution to obtain a desired ratio of red cell volume to storage solution volume (e.g., five pump strokes for red blood cells, followed by two pump strokes for storage solution, and repeating the alternating sequence). This alternating supply of red blood cells and storage solution continues until the weigh scale for the red blood cell collection reservoir 308 indicates that the reservoir 308 is empty.

When the red blood cell collection reservoir 308 is empty, the controller 16 operates the donor interface pumps PP3/PP4 to pump additional storage solution through the filter 313 and into the red blood storage containers 307 and 309, to ensure that a desired ratio between storage solution volume and red blood cell volume exists. This also rinses residual red blood cells from the filter 313 into the red blood cell storage containers 307 and 309 to maximize post-filtration percent red blood cell recovery.

The controlled ratio of pump strokes for red blood cells and for storage solution that the controller 16 achieves ensures that the storage solution is always metered in at a constant ratio. Therefore, regardless of the volume of red blood cells collected, the final red blood cell/storage solution hematocrit can be constant.

The alternating supply of red blood cells and storage solution through the filter 313 eliminates the need to first drain the storage solution into the red blood cell collection reservoir 308, which lessens the overall procedure time.

The alternating supply of red blood cells and storage solution through the filter 313 also eliminates the need to manually agitate a red blood cell/storage solution mixture prior to leukofiltration. Due to density differences, when concentrated red blood cells are added to a preservation solution, or vice versa, the preservation solution floats to the top. Poorly mixed, high hematocrit, high viscosity red blood cells lead to reduced flow rates during leukofiltration. Poorly mixed, high hematocrit, high viscosity red blood cell conditions can also lead to hemolysis. By alternating passage of red blood cells and storage solution through the filter 313, mixing occurs automatically without operator involvement.

The alternating supply of red blood cells and storage solution through the filter 313 also eliminates the need to gravity drain the red blood cell product through the leukofilter 313. As a result, filtration can occur in about half the time required for a gravity-drain procedure.

If desired, the controller 16 can monitor weight changes relating to the red blood cell collection reservoir 308 and the red blood cell storage containers 307 and 309, to derive a value reflecting the percent of red blood cells that are recovered after passage through the leukofilter 313. This value can be communicated to the operator, e.g., on the display screen of user the user interface.

The following expression can be used to derive the percent recovery value:

$$\% \text{ Recovery} = [(\text{Bag } A \text{ Vol} + \text{Bag } B \text{ Vol})/\text{RBC Vol} + Adsol)]*100$$

where:
Bag A Vol represents the volume of red blood cells collected the container 307, calculated as follows:
(Wt of Container 307 containing red blood cells(in g)−Container 307 Tare)/1.062 g/ml
Bag B Vol represents the volume of red blood cells collected the container 309, calculated as follows:
(Wt of Container 309 containing red blood cells(in g)−Container 309 Tare)/1.062 g/ml
RBC Vol represents the volume of red blood cells collected in the red blood cell collection reservoir 308, which the controller 16 determines by weight sensing at the end of the procedure.
Adsol represents the volume of red blood cell storage solution added to the during leukofiltration, which is determined by the controller 16 by capacitive sensing during processing.

(i) The Leukofilter

The leukofilter 313 can be variously constructed. In the embodiment illustrated in FIGS. 24A and 24B, the filter comprises a housing 100 inclosing a filtration medium 102 that can comprise a membrane or be made from a fibrous material. The filtration medium 102 can be arranged in a single layer or in a multiple layer stack. If fibrous, the medium 102 can include melt blown or spun bonded synthetic fibers (e.g., nylon or polyester or polypropylene), semi-synthetic fibers, regenerated fibers, or inorganic fibers. If fibrous, the medium 102 removes leukocytes by depth filtration. If a membrane, the medium 102 removes leukocytes by exclusion.

The housing 100 can comprise rigid plastic plates sealed about their peripheries. In the illustrated embodiment, the housing 100 comprises first and second flexible sheets 104 of medical grade plastic material, such as polyvinyl chloride plasticized with di-2-ethylhexyl-phthalate (PVC-DEHP). Other medical grade plastic materials can be used that are not PVC and/or are DEHP-free.

In the illustrated embodiment, a unitary, continuous peripheral seal 106 (see FIG. 24B) is formed by the application of pressure and radio frequency heating in a single process to the two sheets 104 and filtration medium 102. The seal 106 joins the two sheets 104 to each other, as well as joins the filtration medium 102 to the two sheets 104. The seal 106 integrates the material of the filtration medium 102 and the material of the plastic sheets 104, for a reliable, robust, leak-proof boundary. Since the seal 106 is unitary and continuous, the possibility of blood shunting around the periphery of the filtration medium 102 is eliminated.

The filter 313 also includes inlet and outlet ports 108. The ports 108 can comprise tubes made of medical grade plastic material, like PVC-DEHP. In the embodiment shown in FIG. 24, the ports 108 comprise separately molded parts that are heat sealed by radio frequency energy over a hole 109 formed in the sheets 104 (see FIG. 24B).

Figure 25A:
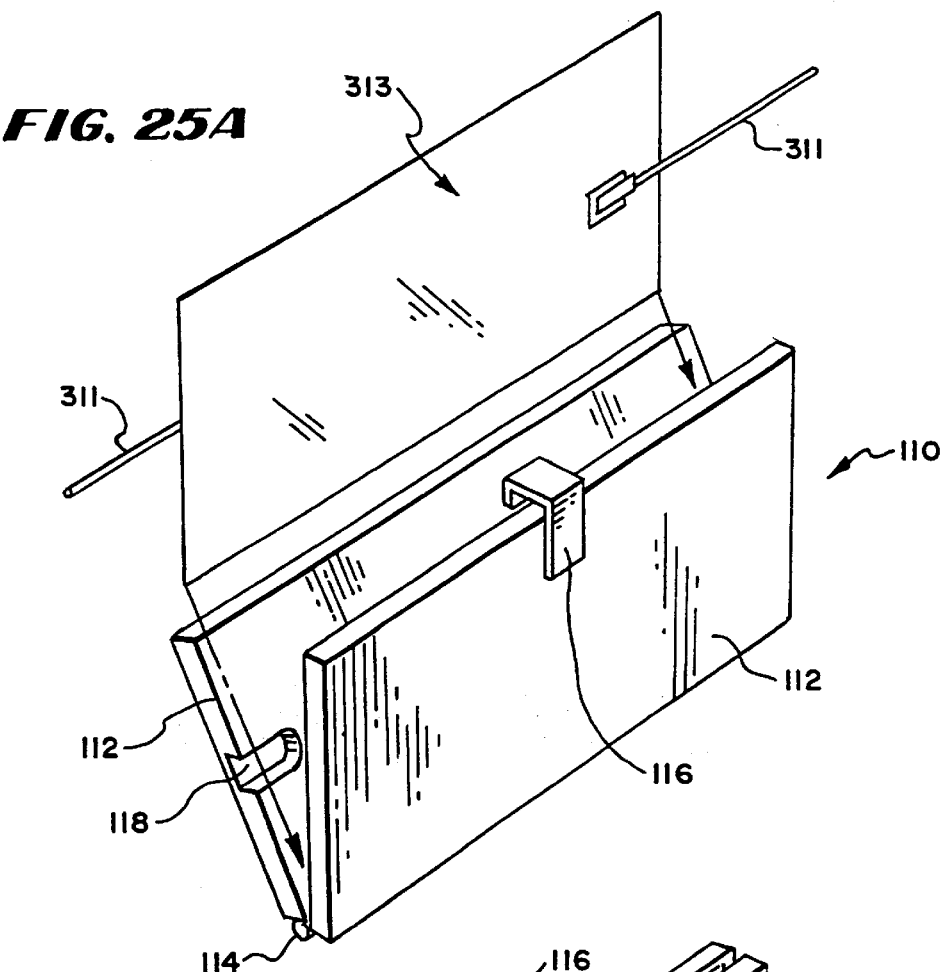
FIGS. 25A and 25B are perspective views of the leukofilter shown in FIG. 24B in association with a fixture that retains the leukofilter during use, FIG. 25A showing the leukofilter being inserted into an opened fixture and FIG. 25B showing the leukofilter retained for use within a closed fixture.
Figure 25B:
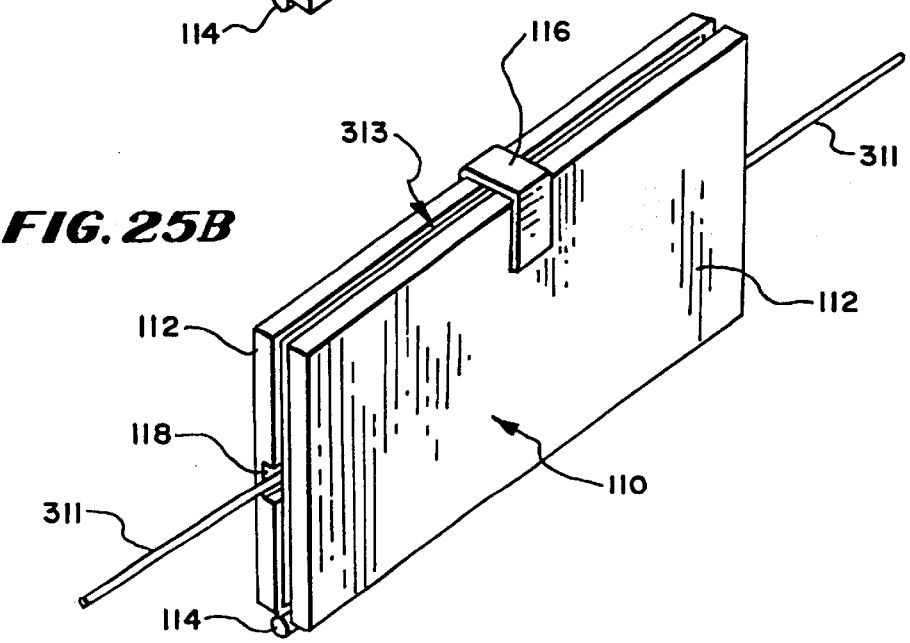

In the illustrated embodiment (as FIGS. 25A and 25B show), the filter 313 is desirably placed within a restraining fixture 110 during use. The fixture 110 restrains expansion of the flexible sheets 104 of the filter housing 100 as a result of pressure applied by pumping red blood cells through the filter 313. The fixture 110 keeps the total blood volume in the filter 313 at a minimum through the filtration process, thereby decreasing filtration time, as well as increasing the red blood cell recovery percentage following leukofiltration.

The fixture 110 can take various forms. In the illustrated embodiment, the fixture 110 comprises two plates 112 coupled by a hinge 114. The fixture 110 can be placed in an open condition (as FIG. 25A shows) to receive the filter 313 prior to leukofiltration, or to remove the filter 313 following leukofiltration. The fixture 110 can also be placed in a closed condition (as FIG. 25B shows) to sandwich the filter 313 between the two plates 112. A releasably latch 116 holds the plates 112 in the closed condition for use.

The plates 112 maintain a desired gap clearance, thereby restraining expansion of the filter 313 during use. The gap clearance is selected to maintain a desired blood flow rate at a desired minimum blood volume.

The plates 112 desirably include indentations 118 in which the ports 108 of the filter 313 rest in a non-occluded condition when the fixture 110 is closed. The interior surfaces of the plates 112 may be roughed or scored with a finish to aid blood flow through the filter 313 when the fixture 110 is closed.

Figure 27:
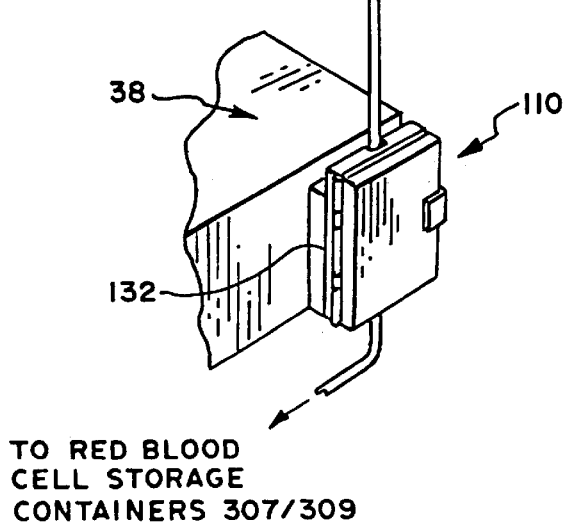
FIG. 27 is a partial perspective view of a side of the base of a device of a type shown in FIGS. 1 and 2, showing a holder for supporting the leukofilter retaining fixture shown in FIGS. 25A and 252 during fluid processing operations.
Figure 28:
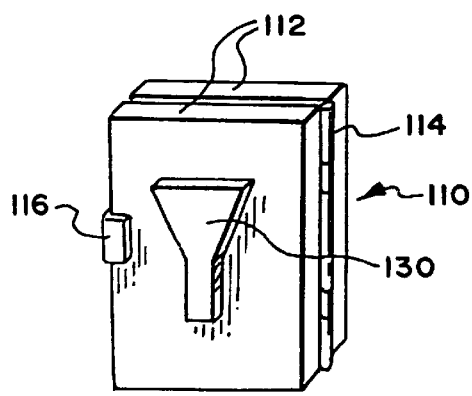
FIG. 28 is a view of one side of the leukofilter retaining fixture of a type shown in FIGS. 25A and 25B, showing a mounting bracket that can be used to secure the leukofilter either to the lid-mounted receptacle shown in FIG. 26 or the base-mounted holder shown in FIG. 27.

The fixture 110 can be made as a stand-alone item that can be separately stored prior to use. It can be stored in association with the device 14 during transport and prior to use, e.g., in a receptacle 128 formed on the exterior of the lid 40 of the device 14 (see FIG. 26). The fixture 110 can include a mounting bracket 130 (see FIG. 28) that, e.g., slidably engages a mating mounting track 132, to hold the fixture 110 in the receptacle 128 prior to use (shown in phantom lines in FIG. 26) or to secure the fixture 110 on the base 38 as leukofiltration is carried out (see FIG. 27).

It should be appreciated that pump-assisted leukofiltration of red blood cells, whole blood, or other blood cell products, wherein blood flow through a leukofilter is not driven strictly by gravity flow, can be carried out using manual or automated systems having configurations different than those shown in this Specification. For example, external peristaltic or fluid actuated pumping devices can be used to transfer whole blood or manually processed blood products from separation bags into processing or storage containers through intermediate leukofiltration devices. It should also be appreciated that a filter restraining fixture of the type shown in FIG. 24B can also be used in association with any pump-assisted leukofiltration system. It should also be appreciated that a filter restraining fixture 110 can also be used in systems where blood flow through the leukofilter relies strictly upon gravity flow.

The many features of the invention have been demonstrated by describing their use in separating whole blood into component parts for storage and blood component therapy. This is because the invention is well adapted for use in carrying out these blood processing procedures. It should be appreciated, however, that the features of the invention equally lend themselves to use in other blood processing procedures.

For example, the systems and methods described, which make use of a programmable cassette in association with a blood processing chamber, can be used for the purpose of washing or salvaging blood cells during surgery, or for the purpose of conducting therapeutic plasma exchange, or in any other procedure where blood is circulated in an extracorporeal path for treatment.

Features of the invention are set forth in the following claims.

We claim:

1. A blood processing system comprising
a blood processing set including
a donor flow channel to convey blood from a donor, a blood processing flow channel including a blood separation chamber to centrifugally separate blood cells from donor whole blood, and a blood component collection flow channel including a blood cell storage container and an in-line filter to remove leukocytes from the blood cells before entering the blood cell storage container, the in-line filter including a filter medium and a flexible housing enclosing the filter medium,
a blood processing device mounted in a case sized to enable hand transport, the blood processing device including
a pump station adapted to be placed into communication with the donor flow channel, the blood processing flow channel, and the blood component collection flow channel,
a centrifuge station adapted to support the blood separation chamber and to rotate the blood separation chamber, and
a controller to operate the pump station in multiple modes, including a processing mode, during which the pump station is operated to convey whole blood in the donor flow channel into the blood processing flow channel for separation of the blood cells in the blood separation chamber, and a collection mode, during which the pump station is operated to convey at least some of the blood cells in the blood processing flow channel into the blood component collection flow channel for on-line removal of leukocytes and collection in the blood cell storage container,
a fixture to restrain expansion of the filter housing during operation of the pump station in the collection mode, the fixture including a bracket, the case including a receptacle mating with the bracket to hold the fixture and enable releasable attachment of the fixture to the case.

2. A blood processing system comprising
a blood processing set including
a donor flow channel to convey blood from a donor, a blood processing flow channel including a blood separation chamber to centrifugally separate blood cells from donor whole blood, and a blood component collection flow channel including a blood cell storage container and an in-line filter to remove leukocytes from the blood cells before entering the blood cell storage container, the in-line filter including a filter medium and a flexible housing enclosing the filter medium,
a blood processing device including a base and a lid hinged to the base, the blood processing device including
a pump station adapted to be placed into communication with the donor flow channel, the blood processing flow channel, and the blood component collection flow channel,
a centrifuge station adapted to support the blood separation chamber and to rotate the blood separation chamber, and
a controller to operate the pump station in multiple modes, including a processing mode, during which the pump station is operated to convey whole blood in the donor flow channel into the blood processing flow channel for separation of the blood cells in the blood separation chamber, and a collection mode, during which the pump station is operated to convey at least some of the blood cells in the blood processing flow channel into the blood component collection flow channel for on-line removal of leukocytes and collection in the blood cell storage container,
a fixture to restrain expansion of the filter housing during operation of the pump station in the collection mode, the fixture including a bracket, the base including a holder mating with the bracket to hold the fixture and enable releasable attachment of the fixture to the base.

3. A blood processing system comprising a blood processing set including
- a donor flow channel to convey blood from a donor, a blood processing flow channel including a blood separation chamber to centrifugally separate blood cells from donor whole blood, and a blood component collection flow channel including a blood cell storage container and an in-line filter to remove leukocytes from the blood cells before entering the blood cell storage container, the in-line filter including a filter medium and a flexible housing enclosing the filter medium, a blood processing device including a base and a lid hinged to the base, the blood processing device including
- a pump station adapted to be placed into communication with the donor flow channel, the blood processing flow channel, and the blood component collection flow channel,
- a centrifuge station adapted to support the blood separation chamber and to rotate the blood separation chamber, and
- a controller to operate the pump station in multiple modes, including a processing mode, during which the pump station is operated to convey whole blood in the donor flow channel into the blood processing flow channel for separation of the blood cells in the blood separation chamber, and a collection mode, during which the pump station is operated to convey at least some of the blood cells in the blood processing flow channel into the blood component collection flow channel for on-line removal of leukocytes and collection in the blood cell storage container, a fixture to restrain expansion of the filter housing during operation of the pump station in the collection mode, the fixture including a bracket, the lid including a receptacle mating with the bracket to hold the fixture and enable releasable attachment of the fixture to the lid.

4. A system according to claim 1 or 2 or 3 wherein the controller includes a function to derive a value reflecting volume of blood cells present in the blood cell storage container after passage through the filter as a percentage of volume of blood cells conveyed to the filter.

5. A system according to claim 1 or 2 or 3 wherein the pump station includes a fluid pressure actuated pump and an actuator to apply fluid pressure to the pump.

6. A system according to claim 1 or 2 or 3 wherein the blood cells comprise red blood cells.

* * * * *